(12) United States Patent
Wellman et al.

(10) Patent No.: US 8,268,795 B2
(45) Date of Patent: Sep. 18, 2012

(54) EMERGENCE OF A R-TYPE CA2+ CHANNEL (CAV 2.3) CONTRIBUTES TO CEREBRAL ARTERY CONSTRICTION FOLLOWING SUBARACHNOID HEMORRHAGE

(75) Inventors: George C. Wellman, Jeffersonville, VT (US); Masanori Ishiguro, Burlington, VT (US)

(73) Assignee: University of Vermont and State Agricultural College, Burlington, VT (US)

( * ) Notice: Subject to any disclaimer, the term of this patent is extended or adjusted under 35 U.S.C. 154(b) by 0 days.

(21) Appl. No.: 12/890,175

(22) Filed: Sep. 24, 2010

(65) Prior Publication Data

US 2011/0086903 A1    Apr. 14, 2011

Related U.S. Application Data

(62) Division of application No. 11/346,614, filed on Feb. 2, 2006, now Pat. No. 7,829,527.

(60) Provisional application No. 60/649,394, filed on Feb. 2, 2005.

(51) Int. Cl.
   *A61K 48/00*    (2006.01)
(52) U.S. Cl. ...... 514/44; 536/24.5; 536/24.31; 536/24.1
(58) Field of Classification Search .................. None
   See application file for complete search history.

(56) References Cited

U.S. PATENT DOCUMENTS 6,653,460 B1    11/2003 Newcomb et al.
7,109,175 B1    9/2006 Bkaily et al.

OTHER PUBLICATIONS

Read et al (Adv. Gen. 53:19-46, 2005).*
Nguyen et al (Curr. Opin. Mol. Ther. 10(2): 158-167, 2008).*
Caplen (Expert Opin. Biol. Ther. 2003, vol. 3, pp. 575-586).*
Check (Nature, 2003, vol. 425, pp. 10-12).*
Arroyo et al., SNX482 selectively blocks P/Q Ca2+ channels and delays the inactivation of Na+ channels of chromaffin cells. Eur J Pharmacol. Aug. 15, 2003;475(1-3):11-8.
Barker et al., Efficacy of prophylactic nimodipine for delayed ischemic deficit after subarachnoid hemorrhage: a metaanalysis. J Neurosurg. Mar. 1996;84(3):405-14.
Ishiguro et al., Enhanced myogenic tone in cerebral arteries from a rabbit model of subarachnoid hemorrhage. Am J Physiol Heart Circ Physiol. Dec. 2002;283(6):H2217-25.
Ishiguro et al., Emergence of a R-type Ca2+ channel (CaV 2.3) contributes to cerebral artery constriction after subarachnoid hemorrhage. Circ Res. Mar. 4, 2005;96(4):419-26.
Ishiguro et al., The emergence of a Ca2+ channel with distinct biophysical properties in cerebral arteries following subarachnoid hemorrahage. Experimental Biology. Washington, D.C. Apr. 17-21, 2004. Abstract 671.15.
Ishiguro et al., Altered Ca2+ channel properties in cerebral arteries following subarachnoid hemorrhage. Experimental Biology: Translating the Genome. San Diego, CA. Apr. 11-15, 2003. Abstract 315.5.
Kuzmiski et al., Topiramate inhibits the initiation of plateau potentials in CA1 neurons by depressing R-type calcium channels. Epilepsia. Apr. 2005;46(4):481-9. Abstract Only.
Newcomb et al., Selective peptide antagonist of the class E calcium channel from the venom of the tarantula Hysterocrates gigas. Biochemistry. Nov. 3, 1998;37(44):15353-62.
Piedras-Rentería et al., Antisense oligonucleotides against alpha1E reduce R-type calcium currents in cerebellar granule cells. Proc Natl Acad Sci U S A. Jun. 23, 1998;95(13):7760-5.
Wellman, Cerebral artery Ca2+ signaling & subarachnoid hemorrhage. Grant Award Date: Nov. 29, 2004. Project Start Date: Dec. 1, 2004. Grant Abstract.

* cited by examiner

*Primary Examiner* — Kimberly Chong
(74) *Attorney, Agent, or Firm* — Wolf, Greenfield & Sacks, P.C.

(57) ABSTRACT

The invention relates to methods and products for treatment of a neurological defect such as a subarachnoid hemorrhage or cerebral vasospasm. Specifically, R-type voltage-gated calcium channel inhibitors and related compositions and kits are described.

15 Claims, 11 Drawing Sheets

Control

SAH

Fig. 2A control

Fig. 2B SAH

**SAH
Anti-Ca$_v$ 2.3**

**Control
Anti-Ca$_v$ 2.3**

**SAH
Anti-Ca$_v$ 2.3
+ Control antigen**

**SAH
No Anti-Ca$_v$ 2.3**

R-type Ca$^{2+}$ channel blocker SNX-482 relieves residual constriction

OxyHb induced gene expression of R-type Ca$^{2+}$ channel α1 subunit

EMERGENCE OF A R-TYPE CA2+ CHANNEL (CAV 2.3) CONTRIBUTES TO CEREBRAL ARTERY CONSTRICTION FOLLOWING SUBARACHNOID HEMORRHAGE

RELATED APPLICATIONS

This application is a divisional of U.S. patent application Ser. No. 11/346,614, filed Feb. 2, 2006, which claims priority under 35 U.S.C. §119(e) to U.S. Provisional Application Ser. No. 60/649,394, filed Feb. 2, 2005, and entitled "EMERGENCE OF A R-TYPE $Ca^{2+}$ CHANNEL ($Ca_v$ 2.3) CONTRIBUTES TO CEREBRAL ARTERY CONSTRICTION FOLLOWING SUBARACHNOID HEMORRHAGE", the contents of each of which are herein incorporated by reference in their entirety.

FEDERALLY SPONSORED RESEARCH

This invention was made with Government support under NIH grant number P20 RR16435 and NHLBI, R01 HL078983. Accordingly, the Government may have certain rights in this invention.

FIELD OF THE INVENTION

The present invention relates to voltage-gated calcium channel inhibitors, such as R- and L-type voltage-gated calcium channel inhibitors, compositions and kits thereof and methods for the use of voltage-gated calcium channel inhibitors in the treatment of diseases such as cerebral vasospasm.

BACKGROUND OF THE INVENTION

Cerebral aneurysm rupture and subarachnoid hemorrhage (SAH) inflict disability and death upon thousands of individuals each year. The consequences of subarachnoid hemorrhage (SAH) following cerebral aneurysm rupture are devastating, with mortality rates as high as 50% and the majority of survivors left with moderate to severe disability (Hop J W, Rinkel G J, Algra A, van Gijn J. *Case-fatality rates and functional outcome after subarachnoid hemorrhage: a systematic review.* Stroke. 1997; 28:660-664). Cerebral vasospasm, characterized as a delayed and sustained arterial constriction, is a major contributor to these high morbidity and mortality rates associated with SAH and current therapies in the treatment of this phenomenon are less than ideal (Dietrich H H, Dacey R G, Jr. *Molecular keys to the problems of cerebral vasospasm.* Neurosurgery. 2000; 46:517-530; Macdonald R L, Weir B K. *A review of hemoglobin and the pathogenesis of cerebral vasospasm.* Stroke. 1991; 22:971-982; Treggiari-Venzi M M, Suter P M, Romand J A. *Review of medical prevention of vasospasm after aneurysmal subarachnoid hemorrhage: a problem of neurointensive care.* Neurosurgery. 2001; 48:249-261.). In addition to vasospasm in large diameter arteries, enhanced constriction of resistance arteries within the cerebral vasculature may contribute to decreased cerebral blood flow and the development of delayed neurological deficits following SAH. Classically, cerebral vasospasm has been diagnosed in SAH patients by the use of angiography to detect cerebral artery narrowing.

In vitro, elevation of intravascular pressure within a physiological range (60 to 100 mmHg) constricts small diameter cerebral arteries in the absence of other vasoactive stimuli. In cerebral arteries from healthy animals, increased intravascular pressure leads to vascular smooth muscle membrane potential depolarization and increased global cytosolic free $Ca^{2+}$ concentration ($[Ca^{2+}]_i$) due to an increase in the open-state probability of L-type voltage-dependent $Ca^{2+}$ channels (VDCCs) (Brayden J E, Wellman G C. *J Cereb Blood Flow Metab.* 1989; 9:256-263; Harder D R. *Circ Res.* 1984; 55:197-202; Knot H J, et. al., *J Physiol (Lond).* 1998; 508: 199-209.). L-type VDCC antagonists cause a maximal decrease in $[Ca^{2+}]_i$ and abolish pressure- and agonist-induced constriction in small diameter arteries (Knot H J, et. al., *J Physiol (Lond).* 1998; 508:199-209; Gokina N I, Knot H J, Nelson M T, Osol G. *Am J Physiol.* 1999; 277:H1178-H1188; Hill M A, et. al., *J Appl Physiol.* 2001; 91:973-983.). While L-type $Ca^{2+}$ channels are widely accepted to be the dominant type of voltage-dependent $Ca^{2+}$ channels expressed in arterial myocytes, studies have also reported the presence of T-type (Chen C C, et. al., *Science.* 2003; 302:1416-1418; Hansen P B, et. al., *Circ Res.* 2001; 89:630-638.), P/Q-type (Hansen P B, et. al., *Circ Res.* 2000; 87:896-902) and nifedipine-resistant high voltage-activated $Ca^{2+}$ Channels (Itonaga Y, et. al., *Life Sci.* 2002; 72:487-500; Morita H, et. al., *Circ Res.* 1999; 85:596-605; Simard J M. *Pflugers Arch.* 1991; 417:528-536.). Expression of L-type $Ca^{2+}$ channels in vascular smooth muscle has been reported to change both during development (Blood A B, et. al., *Am J Physiol Regul Integr Comp Physiol.* 2002; 282:R131-R13) and hypertension (Pratt P F, et. al., *Hypertension.* 2002; 40:214-219.).

SUMMARY OF THE INVENTION

One aspect of the invention is a method for treating cerebral vasospasm by administering to a subject an effective amount for treating cerebral vasospasm of a R-type voltage-dependent calcium channel inhibitor.

In one embodiment of the invention the R-type voltage-dependent calcium channel inhibitor is administered to a subject in conjunction with an L-type voltage-dependent calcium channel inhibitor. In some embodiments the L-type voltage dependent calcium channel inhibitor is an antisense oligonucleotide.

In another embodiment of the invention, the R-type voltage-dependent calcium channel inhibitor is administered within 96 hours after subarachnoid hemorrhage has occurred. In still another embodiment, the R-type voltage-dependent calcium channel inhibitor is administered within 1 week after subarachnoid hemorrhage has occurred. In yet another embodiment, the R-type voltage-dependent calcium channel inhibitor is administered during surgery to treat subarachnoid hemorrhage. In another embodiment of the invention, the R-type voltage-dependent calcium channel inhibitor is an activity inhibitor. For example, some inhibitors of activity are small molecule inhibitors or peptide inhibitors. In yet another embodiment the activity inhibitor is SNX-482. In another embodiment of the invention the R-type voltage-dependent calcium channel inhibitor is an expression inhibitor. For example, an antisense oligonucleotide or siRNA molecule. In one embodiment of the invention the R-type voltage-dependent calcium channel inhibitor is administered orally. Other embodiments of the invention include administration of the R-type voltage-dependent calcium channel inhibitor intravenously, by intrathecal route, by direct bronchial application, by a suppository, and during surgery.

In some embodiments the subject does not have symptoms of cerebral vasospasm. In other embodiments the subject has symptoms of cerebral vasospasm.

Optionally the R-type voltage dependent calcium channel inhibitor is administered by infusion into cerebrospinal fluid. In some embodiments the R-type voltage dependent calcium channel inhibitor is an antisense oligonucleotide.

In another aspect, the invention is a method for treating cerebral vasospasm, by administering to a subject in need thereof an effective amount for treating cerebral vasospasm of a L-type voltage-dependent calcium channel inhibitor, wherein the L-type voltage dependent calcium channel inhibitor is an antisense oligonucleotide of a L-type VDCC smooth muscle splice variant. Optionally the L-type VDCC smooth muscle splice variant is CaV1.2 Exon 9 region.

Another aspect of the invention is a composition of an R-type voltage-dependent calcium channel inhibitor and an anti-cerebral vasospasm drug formulated with a pharmaceutically-acceptable carrier. In one embodiment of the invention, the R-type voltage-dependent calcium channel inhibitor is an activity inhibitor. In another embodiment the activity inhibitor is SNX-482. In still another embodiment of the invention, the R-type voltage-dependent calcium channel inhibitor is an expression inhibitor, for example, an antisense oligonucleotide or siRNA molecule. In still another embodiment of the invention, the composition is formulated for oral administration. In still another embodiment the composition is formulated for intravenous administration. In another embodiment of the invention the anti-cerebral vasospasm drug is an L-type voltage-dependent calcium channel inhibitor. Some examples of L-type voltage-dependent calcium channel inhibitors are diltiazem, a dihydropyridine such as nisoldipine, nicardipine or nifedipine, or a phenylalkalamine such as verapamil.

Another aspect of the invention is a container housing an R-type voltage-dependent calcium channel inhibitor and instructions for administering the R-type voltage-dependent calcium channel inhibitor to a subject having a neurological defect such as a subarachnoid hemorrhage or cerebral vasospasm.

Another aspect of the invention is an R-type voltage-dependent calcium channel inhibitor and a pharmaceutically-acceptable carrier formulated as a suppository.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

BRIEF DESCRIPTION OF DRAWINGS

This application includes examples which refer to figures or other drawings. It is to be understood that the referenced figures are illustrative only and are not essential to the enablement of the claimed invention.

FIG. 1 shows graphs depicting the diameter of cerebral arteries isolated from control and SAH rabbits.

FIG. 2 shows graphs measuring voltage-dependent $Ca^{2+}$ channel (VDCC) currents in native cerebral artery myocytes isolated from control (■) and SAH (●) animals. FIGS. 2A and 2B show patch clamp electrophysiology. Conventional whole-cell patch clamp electrophysiology was used to measure inward currents elicited by 800 ms depolarizing voltage steps from a holding potential of −80 mV with 10 mmol/L $Ba^{2+}$ as the charge carrier. Cell capacitance was 13.6 pF (control) and 19.7 pF (SAH). The y-axis represents current in picoamps (pA) and the x-axis represent time in milliseconds.

FIG. 3 is a series of graphs depicting inactivation of VDCC currents in cerebral artery myocytes isolated from control (■) and SAH (●) animals.

FIG. 4 is a series of graphs showing pharmacology of VDCC currents from control and SAH myocytes.

FIG. 5 is a series of graphs showing the effects of SNX-482 on VDCC currents and arterial diameter.

FIG. 6 shows images of western blots measuring R-type VDCC $Ca_v 2.3$ expression in cerebral arteries following SAH.

FIG. 7 is a series of images showing immunofluorescent labeling of $Ca_v$ 2.3 in cerebral arteries following SAH.

FIG. 8 shows the normalized constriction profiles of the cultured arteries upon treatment with diltiazem at different time points. All samples were constricted by increasing the extracellular concentration of $K^+$ to 60 mM, prior to addition of diltiazem.

FIG. 11 shows two images of the results of PCR reactions to identify mRNA of CaV2.3 in cultured arteries. The results of the PCR reaction are shown on agarose gels.

DETAILED DESCRIPTION

Figure 1A:
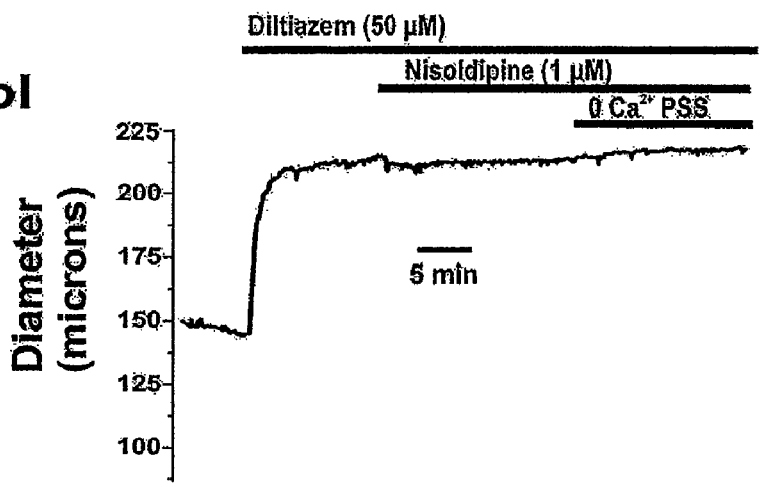
FIGS. 1A and 1B are graphs showing the effect of L-type voltage-gated calcium channel (VDCC) antagonists (inhibitors) on artery diameter. The y-axis is diameter in microns, and the x-axis is time in minutes.

Cerebral artery vasospasm often follows aneurismal or traumatic subarachnoid hemorrhage (SAH). Vasospasm is characterized by sustained and delayed cerebral artery constriction and disrupts autoregulation and reduces optimal perfusion to brain tissue, leading to ischemia. Classically, cerebral artery vasospasm has been diagnosed using angiography. Large diameter arteries have been implicated in contributing to decreased blood flow resulting from SAH. However, small diameter arteries, below the resolution limits of standard angiography, may also be affected by subarachnoid blood. Small diameter (100-200 μm diameter) cerebral arteries from a rabbit model of SAH are significantly more constricted at physiological intravascular pressures compared to similar arteries from healthy animals. This enhanced pressure-induced constriction of small diameter arteries may contribute to decreased cerebral blood flow following SAH.

The invention is based in part on the discovery that such small diameter arteries have R-type voltage dependent calcium channels that are involved in regulating calcium flow and play an important role in decreased cerebral blood flow observed following SAH. To a great extent, the concentration of intracellular free calcium ions ($[Ca^{2+}]_i$) determines the contractile state of vascular smooth muscle, and thus, cerebral artery diameter which is a key component in the regulation of global and local cerebral blood flow. Thus, it has been discovered that SAH leads to enhanced $Ca^{2+}$ entry in myocytes of small diameter cerebral arteries through the emergence of R-type voltage-dependent $Ca^{2+}$ channels (VDCCs) encoded by the gene $Ca_v$ 2.3.

As shown in the Examples section, in vitro diameter measurements and patch clamp electrophysiology demonstrate that L-type VDCC antagonists abolish cerebral artery constriction and block VDCC currents in cerebral artery myocytes from healthy animals. However, five days following the intracisternal injection of blood into rabbits to mimic SAH, cerebral artery constriction and VDCC currents were enhanced and partially resistant to L-type VDCC antagonists. Further, an antagonist of R-type $Ca^{2+}$ channels, reduced constriction and membrane currents in cerebral arteries from SAH animals, but was without effect on cerebral arteries of healthy animals. Consistent with the biophysical and functional data, cerebral arteries from healthy animals express only L-type VDCCs ($Ca_v$ 1.2), whereas following SAH, cerebral arteries were found to express both $Ca_v$ 1.2 and $Ca_v$ 2.3. R-type VDCCs may contribute to enhanced cerebral artery constriction following SAH. These R-type VDCCs thus represent an important therapeutic target in the treatment of neurological deficits following SAH. More detail on these experiments is provided in the examples section below.

Thus, the invention in one aspect relates to a method of treating neurological deficits following SAH, such as cerebral vasospasm by administering to a subject in need thereof an effective amount of an R-type VDCC inhibitor. An R-type voltage-dependent calcium channel inhibitor as used herein as a calcium entry blocking drug whose main pharmacological effect is to prevent or slow the entry of calcium into cells via R-type voltage-gated calcium channels. Cav2.3 is the principal pore-forming unit of R-type voltage-dependent calcium channels identified herein as being expressed in neurons.

The methods of the invention are useful for treating a subject in need thereof. A subject in need thereof is a subject having or at risk of having cerebral vasospasm. In its broadest sense, the terms "treatment" or "to treat" refer to both therapeutic and prophylactic treatments. If the subject in need of treatment is experiencing a condition (i.e., has or is having a particular condition), then "treating the condition" refers to ameliorating, reducing or eliminating one or more symptoms associated with the disorder. If the subject in need of treatment is one who is at risk of having a condition, then treating the subject refers to reducing the risk of the subject having the condition.

A subject having a cerebral vasospasm is one who has symptoms of or has been diagnosed with cerebral vasospasm. A subject at risk of cerebral vasospasm is one who has one or more predisposing factors to the development of cerebral vasospasms. An example of a predisposing factor is existence of a subarachnoid hemorrhage. A subject who has experienced a recent subarachnoid hemorrhage is at significantly higher risk of developing cerebral vasospasm than a subject who has not had a recent subarachnoid hemorrhage. In some embodiments the subject is free of disorders otherwise calling for treatment with R-Type calcium channel inhibitors. In one embodiment such a disorder is a convulsion.

As used herein, a subject includes humans, non human primates, dogs, cats, sheep, goats, cows, pigs, horses and rodents. In preferred embodiments, the subject is human.

The invention provides methods and compositions to treat conditions which would benefit from, and which thus can be treated by, an inhibition of vasoconstriction, such as subarachnoid hemorrhage and preferably cerebral vasospasm.

Agents useful for increasing arterial blood flow, inhibiting vasoconstriction or inducing vasodilation are agents which inhibit voltage-dependent calcium channels such as R-type voltage-dependent calcium channels (R-type VDCC) or L-type VDCC. These inhibitors embrace compounds which are R-type VDCC antagonists. Such inhibitors are referred to as activity inhibitors or R-Type VDCC activity inhibitors. As used herein, an activity inhibitor is an agent which interferes with or prevents the activity of an R-type VDCC. An activity inhibitor may interfere with the ability of the R-type VDCC to bind an agonist. An activity inhibitor may be an agent which competes with a naturally occurring activator of R-type VDCC for interaction with the activation binding site on the R-type VDCC. Alternatively, the activity inhibitor may bind to the R-type VDCC at a site distinct from the activation binding site, but in doing so, it may, for example, cause a conformational change in the R-type VDCC which is transduced to the activation binding site, thereby precluding binding of the natural activator. Alternatively, an activity inhibitor may interfere with a component upstream or downstream of the R-type VDCC but which interferes with the activity of the R-type VDCC. This latter type of activity inhibitor is referred to as a functional antagonist.

An example of an R-type VDCC inhibitor which is an activity inhibitor is SNX-482. "SNX-482" is a peptide inhibitor of R-type voltage-gated calcium channels. SNX-482 can be isolated from the venom of the African tarantula, *Hysterocrates gigas*. The peptide acts at presynaptic sites and selectively inhibits the activity of R-type ($\alpha_1 E$) $Ca^{2+}$ channel with high affinity and in a voltage-dependent manner. Structurally, SNX-482 has a similar size and cysteine disulfide bond arrangement with two other spider toxins, hanatoxin (which can inhibit voltage-gated potassium channels) and gramotoxin SIA (an inhibitor of voltage gated calcium channels isolated from the venom of Chilean tarantula *Grammostola spatulata* or *Phrixotrichus spatulata*), that selectively block calcium channels by altering their gating. Conserved residues necessary for inhibitory function include cysteine residues necessary for forming disulfide bridges that confer the tertiary structure of the peptide. An example of the sequence for SNX-482 is H-Gly-Val-Asp-Lys-Ala-Gly-Cys-Arg-Tyr-Met-Phe-Gly-Gly-Cys-Ser-Val-Asn-Asp-Asp-Cys-Cys-Pro-Arg-Leu-Gly-Cys-His-Ser-Leu-Phe-Ser-Tyr-Cys-Ala-Trp-Asp-Leu-Thr-Phe-Ser-Asp-OH (SEQ ID NO:5).

One of skill in the art will recognize that conservative amino acid substitutions may be made without affecting structure and function of SNX-482. As used herein, a "conservative amino acid substitution" or "conservative substitution" refers to an amino acid substitution in which the substituted amino acid residue is of similar charge as the replaced residue and is of similar or smaller size than the replaced residue. Conservative substitutions of amino acids include substitutions made amongst amino acids within the following groups: (a) the small non-polar amino acids, A, M, I, L, and V; (b) the small polar amino acids, G, S, T and C; (c) the amido amino acids, Q and N; (d) the aromatic amino acids, F, Y and W; (e) the basic amino acids, K, R and H; and (f) the acidic amino acids, E and D. Substitutions which are charge neutral and which replace a residue with a smaller residue may also be considered "conservative substitutions" even if the residues are in different groups (e.g., replacement of phenylalanine with the smaller isoleucine). The term "conservative amino acid substitution" also refers to the use of amino acid analogs or variants. A conservative amino acid substitution in the SNX-482 sequence would not include replacement of all cysteine residues.

Other agents which are useful according to the methods of the invention in the treatment of conditions described herein include agents which interfere with R-type VDCC expression at either the mRNA or protein level. Such inhibitors are referred to as expression inhibitors or R-type VDCC expression inhibitors. Examples of expression inhibitors include antisense oligonucleotides and therapeutic RNA.

Thus, the invention embraces antisense oligonucleotides that selectively bind to a nucleic acid molecules encoding an R-type VDCC to decrease expression and activity of this protein and subunits thereof. Antisense oligonucleotides can be designed to interfere with expression of the R-type VDCC based on the known nucleotides sequence of the R-type VDCC. For instance, the following oligonucleotides are useful as antisense oligonucleotide inhibitors of the rabbit R-type VDCC:

```
5'-CCACCTGTGCTGTCCCTGCCAC-3'     (SEQ ID NO: 14)
                                 22mer (7056-7035)

5'-ACTCGGGCCAGCCAGCTCCCTCCAC-3'  (SEQ ID NO: 15)
                                 25mer (7695-7671)

5'-GCCAGACCCTCCCTTCCC-3'         (SEQ ID NO: 16)
                                 18mer (7634-7617)

5'-ACTCAGCAGGTCGCCCACAGCGCCAC-3' (SEQ ID NO: 17)
                                 26mer (7354-7329)

5'-GCCATCTGCATGCTGCTCT-3'        (SEQ ID NO: 18)
                                 19mer (3655-3637)

5'-GCCAGCCATGGCGGCTCCC-3'        (SEQ ID NO: 19)
                                 19mer (3225-3207)
```

The invention also embraces antisense oligonucleotides that selectively bind to a nucleic acid molecules encoding an L-type VDCC to decrease expression and activity of this protein and subunits thereof, particularly the splice variants that are found in smooth muscle arteries. Antisense oligonucleotides can be designed to interfere with expression of the L-type VDCC based on the known nucleotides sequence of the L-type VDCC. For instance, the following oligonucleotides are useful as antisense oligonucleotide inhibitors of the rabbit L-type VDCC smooth muscle splice variants (CaV1.2 Exon 9 region): 5'-AAGCCCGCTGGAGTGCCTCT-3' (SEQ ID NO:20). An antisense strand sequence targeting a common region of Rabbit CaV 1.2 is 5'-CTCTTCCAGCTGCTGCTTCTCCC-3' (SEQ ID NO:21).

Similar oligonucleotides for the human R- and L-type VDCC may easily be identified. For instance oligonucleotides can be developed against the human genes using the criteria described below, such as optimal length and stabilization. Additional criteria include selection of positive motifs such as: CCAC, TCCC, ACTC, GCCA, CTCT and exclusion of negative motifs such as: GGGG, ACTG, AAA, TAA.

As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense oligonucleotide molecules are designed so as to interfere with transcription or translation of a target gene upon hybridization with the target gene or transcript. Antisense oligonucleotides that selectively bind to a nucleic acid molecule encoding an R-type VDCC are particularly preferred. Those skilled in the art will recognize that the exact length of the antisense oligonucleotide and its degree of complementarity with its target will depend upon the specific target selected, including the sequence of the target and the particular bases which comprise that sequence.

It is preferred that the antisense oligonucleotide be constructed and arranged so as to bind selectively with the target under physiological conditions, i.e., to hybridize substantially more to the target sequence than to any other sequence in the target cell under physiological conditions. Based upon the nucleotide sequences of nucleic acid molecules encoding R-type VDCC, (e.g., GenBank Accession Nos. NM 009782-R type alpha 1E subunit) or upon allelic or homologous genomic and/or cDNA sequences, one of skill in the art can easily choose and synthesize any of a number of appropriate antisense oligonucleotide molecules for use in accordance with the present invention. In order to be sufficiently selective and potent for inhibition, such antisense oligonucleotides should comprise at least about 10 and, more preferably, at least about 15 consecutive bases which are complementary to the target, although in certain cases modified oligonucleotides as short as 7 bases in length have been used successfully as antisense oligonucleotides. See Wagner et al., Nat. Med. 1(11):1116-1118, 1995. Most preferably, the antisense oligonucleotides comprise a complementary sequence of 20-30 bases. Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted by antisense oligonucleotides. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., Cell Mol. Neurobiol. 14(5):439-457, 1994) and at which proteins are not expected to bind.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acid molecules has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose.

The present invention, thus, contemplates pharmaceutical preparations containing modified antisense oligonucleotide molecules that are complementary to and hybridizable with, under physiological conditions, nucleic acid molecules encoding R-type VDCC, together with pharmaceutically acceptable carriers. Antisense oligonucleotides may be administered as part of a pharmaceutical composition. In this latter embodiment, it may be preferable that a slow intravenous administration be used. Such a pharmaceutical composition may include the antisense oligonucleotides in combination with any standard physiologically and/or pharmaceutically acceptable carriers which are known in the art. The compositions should be sterile and contain a therapeutically effective amount of the antisense oligonucleotides in a unit of weight or volume suitable for administration to a subject.

The methods of the invention also encompass use of isolated short RNA that directs the sequence-specific degradation of R-type VDCC mRNA through a process known as RNA interference (RNAi). The process is known to occur in a wide variety of organisms, including embryos of mammals and other vertebrates. It has been demonstrated that dsRNA is processed to RNA segments 21-23 nucleotides (nt) in length, and furthermore, that they mediate RNA interference in the absence of longer dsRNA. Thus, these 21-23 nt fragments are sequence-specific mediators of RNA degradation and are referred to herein as siRNA or RNAi. Methods of the invention encompass the use of these fragments (or recombinantly produced or chemically synthesized oligonucleotides of the same or similar nature) to enable the targeting of R-type VDCC mRNAs for degradation in mammalian cells useful in the therapeutic applications discussed herein.

The methods for design of the RNA's that mediate RNAi and the methods for transfection of the RNAs into cells and animals is well known in the art and are readily commercially available (Verma N. K. et al, J. Clin. Pharm. Ther., 28(5):395-404 (2004), Mello C. C. et al. Nature, 431(7006)338-42 (2004), Dykxhoorn D. M. et al., Nat. Rev. Mol. Cell Biol. 4(6):457-67 (2003) Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK)). The RNAs are preferably chemically synthesized using appropriately protected ribonucleoside phosphoramidites and a conventional DNA/RNA synthesizer. Most conveniently, siRNAs are obtained from commercial RNA oligo synthesis suppliers listed herein. In general, RNAs are not too difficult to synthesize and are readily provided in a quality suitable for RNAi. A typical 0.2 μmol-scale RNA synthesis provides about 1 milligram of RNA, which is sufficient for 1000 transfection experiments using a 24-well tissue culture plate format.

The R-type VDCC cDNA specific siRNA is designed preferably by selecting a sequence that is not within 50-100 bp of the start codon and the termination codon, avoids intron regions, avoids stretches of 4 or more bases such as AAAA, CCCC, avoids regions with GC content <30% or >60%, avoids repeats and low complex sequence, and it avoids single nucleotide polymorphism sites. The R-type VDCC siRNA may be designed by a search for a 23-nt sequence motif $AA(N_{19})$. If no suitable sequence is found, then a 23-nt sequence motif $NA(N_{21})$ may be used with conversion of the 3' end of the sense siRNA to TT. Alternatively, the R-type VDCC siRNA can be designed by a search for $NAR(N_{17})$ YNN. The target sequence may have a GC content of around 50%. The siRNA targeted sequence may be further evaluated using a BLAST homology search to avoid off target effects on other genes or sequences. Negative controls are designed by scrambling targeted siRNA sequences. The control RNA preferably has the same length and nucleotide composition as the siRNA but has at least 4-5 bases mismatched to the siRNA. The RNA molecules of the present invention can comprise a 3' hydroxyl group. The RNA molecules can be single-stranded or double stranded; such molecules can be blunt ended or comprise overhanging ends (e.g., 5', 3') from about 1 to about 6 nucleotides in length (e.g., pyrimidine nucleotides, purine nucleotides). In order to further enhance the stability of the RNA of the present invention, the 3' overhangs can be stabilized against degradation. The RNA can be stabilized by including purine nucleotides, such as adenosine or guanosine nucleotides. Alternatively, substitution of pyrimidine nucleotides by modified analogues, e.g., substitution of uridine 2 nucleotide 3' overhangs by 2'-deoxythymidine is tolerated and does not affect the efficiency of RNAi. The absence of a 2' hydroxyl significantly enhances the nuclease resistance of the overhang in tissue culture medium.

The RNA molecules used in the methods of the present invention can be obtained using a number of techniques known to those of skill in the art. For example, the RNA can be chemically synthesized or recombinantly produced using methods known in the art. Such methods are described in U.S. Published Patent Application Nos. US2002-0086356A1 and US2003-0206884A1 which are hereby incorporated by reference in their entirety.

The methods described herein are used to identify or obtain RNA molecules that are useful as sequence-specific mediators of R-type VDCC mRNA degradation and, thus, for inhibiting R-type VDCC receptor activity. Expression of the R-type VDCC receptor can be inhibited in humans in order to prevent the disease or condition from occurring, limit the extent to which it occurs or reverse it.

The RNA molecules may also be isolated using a number of techniques known to those of skill in the art. For example, gel electrophoresis can be used to separate RNAs from the combination, gel slices comprising the RNA sequences removed and RNAs eluted from the gel slices. Alternatively, non-denaturing methods, such as non-denaturing column chromatography, can be used to isolate the RNA produced. In addition, chromatography (e.g., size exclusion chromatography), glycerol gradient centrifugation, affinity purification with antibody can be used to isolate RNAs.

Any RNA can be used in the methods of the present invention, provided that it has sufficient homology to the R-type VDCC receptor gene to mediate RNAi. The RNA for use in the present invention can correspond to the entire R-type VDCC receptor gene or a portion thereof. There is no upper limit on the length of the RNA that can be used. For example, the RNA can range from about 21 base pairs (bp) of the gene to the full length of the gene or more. In one embodiment, the RNA used in the methods of the present invention is about 1000 bp in length. In another embodiment, the RNA is about 500 bp in length. In yet another embodiment, the RNA is about 22 bp in length. In certain embodiments the preferred length of the RNA of the invention is 21 to 23 nucleotides.

The inhibitors described herein are isolated molecules. An isolated molecule is a molecule that is substantially pure and is free of other substances with which it is ordinarily found in nature or in vivo systems to an extent practical and appropriate for its intended use. In particular, the molecular species are sufficiently pure and are sufficiently free from other biological constituents of host cells so as to be useful in, for example, producing pharmaceutical preparations or sequencing if the molecular species is a nucleic acid, peptide, or polysaccharide. Because an isolated molecular species of the invention may be admixed with a pharmaceutically-acceptable carrier in a pharmaceutical preparation, the molecular species may comprise only a small percentage by weight of the preparation. The molecular species is nonetheless substantially pure in that it has been substantially separated from the substances with which it may be associated in living systems.

"Subarachnoid hemorrhage" (SAH) is a condition in which blood collects beneath the arachnoid mater, a membrane that covers the brain. This area, called the subarachnoid space, normally contains cerebrospinal fluid. The accumulation of blood in the subarachnoid space can lead to stroke, seizures, and other complications. Additionally, subarachnoid hemorrhages may cause permanent brain damage and a number of harmful biochemical events in the brain. In some instances, subarachnoid hemorrhages include non-traumatic types of hemorrhages, usually caused by rupture of a berry aneurysm or arteriovenous malformation (AVM). Other causes include bleeding from a vascular anomaly and extension into the subarachnoid space from a primary intracerebral hemorrhage. Symptoms of subarachnoid hemorrhage include sudden and severe headache, nausea and/or vomiting, symptoms of meningeal irritation (eg, neck stiffness, low back pain, bilateral leg pain) photophobia and visual changes, and/or loss of consciousness.

Subarachnoid hemorrhage is often secondary to a head injury or a blood vessel defect known as an aneurysm. In some instances, subarachnoid hemorrhage can induce a cerebral vasospasm that may in turn lead to an ischemic stroke. A common manifestation of a subarachnoid hemorrhage is the presence of blood in the CSF.

Subjects having a subarachnoid hemorrhage can be identified by a number of symptoms. For example, a subject having a subarachnoid hemorrhage will present with blood in the subarachnoid, usually in a large amount. Subjects having a subarachnoid hemorrhage can also be identified by an intracranial pressure that approximates mean arterial pressure, by a fall in cerebral perfusion pressure or by the sudden transient loss of consciousness (sometimes preceded by a painful headache). In about half of cases, subjects present with a severe headache which may be associated with physical exertion. Other symptoms associated with subarachnoid hemorrhage include nausea, vomiting, memory loss, hemiparesis and aphasia. Subjects having a subarachnoid hemorrhage can also be identified by the presence of creatine kinase-BB isoenzyme activity in their CSF. This enzyme is enriched in the brain but is normally not present in the CSF. Thus, its presence in the CSF is indicative of "leak" from the brain into the subarachnoid. Assay of creatine-kinase BB isoenzyme activity in the CSF is described by Coplin et al. (Coplin, et al, Arch Neurol, 1999, 56(11):1348-1352) Additionally, a spinal tap or lumbar puncture can be used to demonstrate if there is blood present in the CSF, a strong indication of a subarachnoid hemorrhage. A cranial CT scan or an MRI can also be used to identify blood in the subarachnoid region. Angiography can also be used to determine not only whether a hemorrhage has occurred but also the location of the hemorrhage.

Subarachnoid hemorrhage commonly results from rupture of an intracranial saccular aneurysm or from malformation of the arteriovenous system in, and leading to, the brain. Accordingly, a subject at risk of having a subarachnoid hemorrhage includes subjects having a saccular aneurysm as well as subjects having a malformation of the arteriovenous system. It is estimated that 5% of the population have such aneurysms yet only 1 in 10,000 people actually have a subarachnoid hemorrhage. The top of the basilar artery and the junction of the basilar artery with the superior cerebellar or the anterior inferior cerebellar artery are common sites of saccular aneurysms. Subjects having a subarachnoid hemorrhage may be identified by an eye examination, whereby slowed eye movement may indicate brain damage. A subject with a developing saccular aneurysm can be identified through routine medical imaging techniques, such as CT and MRI. A developing aneurysm forms a mushroom-like shape (sometimes referred to as "a dome with a neck" shape).

A vasospasm is a sudden decrease in the internal diameter of a blood vessel that results from contraction of smooth muscle within the wall of the vessel. Vasospasms result in decreased blood flow, but increased system vascular resistance. It is generally believed that vasospasm is caused by local injury to vessels, such as that which results from atherosclerosis and other structural injury including traumatic head injury. Cerebral vasospasm is a naturally occurring vasoconstriction which can also be triggered by the presence of blood in the CSF, a common occurrence after rupture of an aneurysm or following traumatic head injury. Cerebral vasospasm can ultimately lead to brain cell damage, in the form of cerebral ischemia and infarction, due to interrupted blood supply.

Cerebral vasospasm is characterized by a sudden decrease in the internal diameter of a blood vessel that results from contraction of smooth muscle within the wall of the vessel. This causes a decrease in cerebral blood flow, but an increase in vascular resistance. As used herein, cerebral vasospasm refers to the delayed occurrence of narrowing of large capacity arteries at the base of the brain after subarachnoid hemorrhage, often associated with diminished perfusion in the territory distal to the affected vessel. Cerebral vasospasm can occur any time after rupture of an aneurysm but most commonly peaks at seven days following the hemorrhage and often resolves within 14 days when the blood has been absorbed by the body.

A subject having a vasospasm is a subject who presents with diagnostic markers and symptoms associated with vasospasm. Diagnostic markers include the presence of blood in the CSF and/or a recent history of a subarachnoid hemorrhage. Vasospasm associated symptoms include paralysis on one side of the body, inability to vocalize the words or to understand spoken or written words, and inability to perform tasks requiring spatial analysis. Such symptoms may develop over a few days, or they may fluctuate in their appearance, or they may present abruptly.

MR angiography and CT angiography can be used to diagnose cerebral vasospasm. Angiography is a technique in which a contrast agent is introduced into the blood stream in order to view blood flow and/or arteries. A contrast agent is required because blood flow and/or arteries are sometimes only weakly apparent in a regular MR or CT scan. Appropriate contrast agents will vary depending upon the imaging technique used. For example, gadolinium is a common contrast agent used in MR scans. Other MR appropriate contrast agents are known in the art. Transcranial Doppler ultrasound can also be used to diagnose and monitor the progression of a vasospasm. As mentioned earlier, the presence of blood in the cerebrospinal fluid can be detected using CT scans. However, in some instances where the amount of blood is so small as to not be detected by CT, a lumbar puncture is warranted.

A subject at risk of a vasospasm includes a subject who has detectable blood in the cerebrospinal fluid, or one who has a detectable aneurysm as detected by a CT scan, yet has not begun to experience the symptoms associated with having a vasospasm. A subject at risk of a vasospasm may also one who has experienced a traumatic head injury. Traumatic head injury usually results from a physical force to the head region, in the form of a fall or a forceful contact with a solid object. Subjects at risk of a vasospasm may also include those who have recently (e.g., in the last two weeks or months) experienced a subarachnoid hemorrhage (as described above).

In one aspect of the invention, an R-type VDCC inhibitor is administered to the subject having or at risk of having a vasospasm in an effective amount to treat a vasospasm. An effective amount to treat a vasospasm may be that amount necessary to ameliorate, reduce or eliminate altogether one or more symptoms relating to a vasospasm, preferably including brain damage that results from vasospasm such as an infarct. Brain damage can be measured anatomically using medical imaging techniques to measure infarct sizes. Alternatively or in conjunction, brain damage may be measured functionally in terms of cognitive or sensory skills of the subject.

Inhibitors can be combined with other therapeutic agents, such as an anti-cerebral vasospasm drug. The inhibitor and other therapeutic agent may be administered simultaneously or sequentially. When the other therapeutic agents are administered simultaneously they can be administered in the same or separate formulations, but are administered at the same time. The other therapeutic agents are administered sequentially with one another and with inhibitor, when the administration of the other therapeutic agents and the inhibitor is temporally separated. The separation in time between the administration of these compounds may be a matter of minutes or it may be longer.

Subjects at risk of vasospasm are currently administered a variety of preventative medications including L-type voltage-dependent calcium channel (L-type VDCC) inhibitors (e.g., nimodipine), phenylephrine, dopamine, as well as a combination of mannitol and hyperventilation. Some forms of prophylactic treatments aim to increase the cerebral perfusion pressure. In accordance with the present invention, any of these prophylactic therapies may be co-administered to a subject at risk of having a vasospasm along with the agents of the invention. Thus, other therapeutic agents include but are not limited to anti-cerebral vasospasm drug such as L-type VDCC and a phenylalkalamine such as verapamil, etc.

An L-type voltage-dependent calcium channel inhibitor as used herein as a calcium entry blocking drug whose main pharmacological effect is to prevent or slow the entry of calcium into cells via L-type voltage-gated calcium channels. $\alpha_{2C}$ (Cav1.2) and $\alpha_{1D}$ (Cav1.3) are the two principal pore-forming units of L-type voltage-dependent calcium channels expressed in neurons. $\alpha_{1C}$ (Cav1.2) is also present in cerebral artery myocytes. Examples of L-type calcium channel inhibitors include but are not limited to: dihydropyridine L-type blockers such as nisoldipine, nicardipine and nifedipine, AHF (such as 4aR,9aS)-(+)-4a-Amino-1,2,3,4,4a,9a-hexahydro-4aH-fluorene, HCl), isradipine (such as 4-(4-Benzofurazanyl)-1,-4-dihydro-2,6-dimethyl-3,5-pyridinedicarboxylic acid methyl 1-methylethyl ester), Calciseptin/calciseptine (such as isolated from (Dendroaspis polylepis. ploylepis, H-Arg-Ile-Cys-Tyr-Ile-His-Lys-Ala-Ser-Leu-Pro-Arg-Ala-Thr-Lys-Thr-Cys-Val-Glu-Asn-Thr-Cys-Tyr-Lys-Met-Phe-Ile-Arg-Thr-Gln-Arg-Glu-Tyr-Ile-Ser-Glu-Arg-Gly-Cys-Gly-Cys-Pro-Thr-Ala-Met-Trp-Pro-Tyr-Gln-Thr-Glu-Cys-Cys-Lys-Gly-Asp-Arg-Cys-Asn-Lys-OH (SEQ ID NO:6), Calcicludine (such as isolated from Dendroaspis angusticeps (eastern green mamba)), (H-Trp-Gln-Pro-Pro-Trp-Tyr-Cys-Lys-Glu-Pro-Val-Arg-Ile-Gly-Ser-Cys-Lys-Lys-Gln-Phe-Ser-Ser-Phe-Tyr-Phe-Lys-Trp-Thr-Ala-Lys-Lys-Cys-Leu-Pro-Phe-Leu-Phe-Ser-Gly-Cys-Gly-Gly-Asn-Ala-Asn-Arg-Phe-Gln-Thr-Ile-Gly-Glu-Cys-Arg-Lys-Lys-Cys-Leu-Gly-Lys-OH, SEQ ID NO:7), Cilnidipine (such as also FRP-8653, a dihydropyridine-type inhibitor), Dilantizem (such as (2S, 3S)-(+)-cis-3-Acetoxy-5-(2-dimethylaminoethyl)-2,3-dihydro-2-(4-methoxyphenyl)-1,5-benzothiazepin-4(5H)-one hydrochloride), diltiazem (such as benzothiazepin-4(5H)-one, 3-(acetyloxy)-5-[2-(dimethylamino)ethyl]-2,3-dihydro-2-(4-methoxyphenyl)-,(+)-cis-,monohydrochloride), Felodipine (such as 4-(2,3-Dichlorophenyl)-1,4-dihydro-2,6-dimethyl-3,5-pyridinecarboxylic acid ethyl methyl ester), FS-2 (such as an isolate from Dendroaspis polylepis polylepis venom), FTX-3.3 (such as an isolate from Agelenopsis aperta), Neomycin sulfate (such as $C_{23}H_{46}N_6O_{13}.3H_2SO_4$), Nicardipine (such as 1,4-Dihydro-2,6-dimethyl-4-(3-nitrophenyl)methyl-2-[methyl(phenylmethyl)amino]-3,5-pyridinedicarboxylic acid ethyl ester hydrochloride, also YC-93, Nifedipine (such as 1,4-Dihydro-2,6-dimethyl-4-(2-nitrophenyl)-3,5-pyridinedicarboxylic acid dimethyl ester), Nimodipine (such as 4-Dihydro-2,6-dimethyl-4-(3-nitrophenyl)-3,5-pyridinedicarboxylic acid 2-methoxyethyl 1-methylethyl ester) or (Isopropyl 2-methoxyethyl 1,4-dihydro-2,6-dimethyl-4-(m-nitrophenyl)-3,5-pyridinedicarboxylate), Nitrendipine (such as 1,4-Dihydro-2,6-dimethyl-4-(3-nitrophenyl)-3,5-pyridinedicarboxylic acid ethyl methyl ester), S-Petasin (such as (3S,4aR,5R,6R)-[2,3,4,4a,5,6,7,8-Octahydro-3-(2-propenyl)-4a,5-dimethyl-2-oxo-6-naphthyl]Z-3'-methylthio-1'-propenoate), Phloretin (such as 2',4',6'-Trihydroxy-3-(4-hydroxyphenyl)propiophenone, also 3-(4-Hydroxyphenyl)-1-(2,4,6-trihydroxyphenyl)-1-propanone, also b-(4-Hydroxyphenyl)-2,4,6-trihydroxypropiophenone), Protopine (such as $C_{20}H_{19}NO_5.HCl$), SKF-96365 (such as 1-[b-[3-(4-Methoxyphenyl)propoxy]-4-methoxyphenethyl]-1H-imidazole, HCl), Tetrandine (such as 6,6',7,12-Tetramethoxy-2,2'-dimethylberbaman), (±)-Methoxyverapamil or (+)-Verapamil (such as 5-[N-(3,4-Dimethoxyphenylethyl) methylamino]-2-(3,4-dimethoxyphenyl)-2-isopropylvaleronitrile hydrochloride), and (R)-(+)-Bay K8644 (such as R-(+)-1,4-Dihydro-2,6-dimethyl-5-nitro-4-[2-(trifluoromethyl)phenyl]-3-pyridinecarboxylic acid methyl ester). The foregoing examples may be specific to L-type voltage-gated calcium channels or may inhibit a broader range of voltage-gated calcium channels, e.g. N, P/Q, R, and T-type.

The compositions are delivered in effective amounts. The term effective amount refers to the amount necessary or sufficient to realize a desired biologic effect. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is effective to treat the particular subject. The effective amount for any particular application can vary depending on such factors as the disease or condition being treated, the particular inhibitor being administered, the size of the subject, or the severity of the disease or condition. One of ordinary skill in the art can empirically determine the effective amount of a particular inhibitor and/or other therapeutic agent without necessitating undue experimentation. It is preferred generally that a maximum dose be used, that is, the highest safe dose according to some medical judgment. Multiple doses per day may be contemplated to achieve appropriate systemic levels of compounds. Appropriate system levels can be determined by, for example, measurement of the patient's peak or sustained plasma level of the drug. "Dose" and "dosage" are used interchangeably herein.

Generally, daily oral doses of active compounds will be from about 0.01 milligrams/kg per day to 1000 milligrams/kg per day. It is expected that oral doses in the range of 0.5 to 50 milligrams/kg, in one or several administrations per day, will yield the desired results. Dosage may be adjusted appropriately to achieve desired drug levels, local or systemic, depending upon the mode of administration. For example, it is expected that intravenous administration would be from an order to several orders of magnitude lower dose per day. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of compounds.

For any compound described herein the therapeutically effective amount can be initially determined from preliminary in vitro studies and/or animal models. A therapeutically effective dose can also be determined from human data for inhibitors which have been tested in humans and for compounds which are known to exhibit similar pharmacological activities, such as other related active agents. Higher doses may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the inhibitor can be administered to a subject by any mode that delivers the inhibitor to the desired surface. Administering the pharmaceutical composition of the present invention may be accomplished by any means known to the skilled artisan. Preferred routes of administration include but are not limited to oral, intrathecal, intra-arterial, direct bronchial application, direct infusion into cerebrospinal fluid (CSF), parenteral (e.g. intravenous), intramuscular, intranasal, sublingual, intratracheal, inhalation, ocular, vaginal, and rectal, e.g., using a suppository. The inhibitors and other therapeutics may also be delivered to a subject during surgery to treat the underlying condition such as subarachnoid hemorrhage or during intra-arterial procedures.

In some embodiments direct infusion into CSF is preferred. Delivery of the agents of the invention to the CSF allows the compounds immediate access to cerebral artery myocytes, where they can act on the voltage-dependent calcium channels. This route also limits the exposure of the agent to other body tissues, thus limiting side effects. Administration of antisense oligonucleotides by this route is preferred in some embodiments.

For oral administration, the compounds (i.e., inhibitors, and other therapeutic agents) can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, i.e. EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, 1981, "Soluble Polymer-Enzyme Adducts" In: *Enzymes as Drugs*, Hocenberg and Roberts, eds., Wiley-Interscience, New York, N.Y., pp. 367-383; Newmark, et al., 1982, J. Appl. Biochem. 4:185-189. Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the inhibitor (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the inhibitor (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the inhibitor or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Also contemplated herein is pulmonary delivery of the inhibitors (or derivatives thereof). The inhibitor (or derivative) is delivered to the lungs of a mammal while inhaling and traverses across the lung epithelial lining to the blood stream. Other reports of inhaled molecules include Adjei et al., 1990, Pharmaceutical Research, 7:565-569; Adjei et al., 1990, International Journal of Pharmaceutics, 63:135-144 (leuprolide acetate); Braquet et al., 1989, Journal of Cardiovascular Pharmacology, 13(suppl. 5):143-146 (endothelin-1); Hubbard et al., 1989, Annals of Internal Medicine, Vol. III, pp. 206-212 (a1-antitrypsin); Smith et al., 1989, J. Clin. Invest. 84:1145-1146 (a-1-proteinase); Oswein et al., 1990, "Aerosolization of Proteins", Proceedings of Symposium on Respiratory Drug Delivery II, Keystone, Colo., March, (recombinant human growth hormone); Debs et al., 1988, J. Immunol. 140:3482-3488 (interferon-g and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of inhibitor (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified inhibitor may also be prepared in different formulations depending on the type of chemical modification or the type of device employed.

Formulations suitable for use with a nebulizer, either jet or ultrasonic, will typically comprise inhibitor (or derivative) dissolved in water at a concentration of about 0.1 to 25 mg of biologically active inhibitor per mL of solution. The formulation may also include a buffer and a simple sugar (e.g., for inhibitor stabilization and regulation of osmotic pressure). The nebulizer formulation may also contain a surfactant, to reduce or prevent surface induced aggregation of the inhibitor caused by atomization of the solution in forming the aerosol.

Formulations for use with a metered-dose inhaler device will generally comprise a finely divided powder containing the inhibitor (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing inhibitor (or derivative) and may also include a bulking agent, such as lactose, sorbitol, sucrose, or mannitol in amounts which facilitate dispersal of the powder from the device, e.g., 50 to 90% by weight of the formulation. The inhibitor (or derivative) should most advantageously be prepared in particulate form with an average particle size of less than 10 mm (or microns), most preferably 0.5 to 5 mm, for most effective delivery to the distal lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides. Suppositories are a solid dosage form of medication that can be delivered internally to a patient, human or animal by insertion of the solid dosage form directly to the an area of the body. Known types of suppositories include rectal, vaginal and urethral suppositories. Commonly used bases, which are commercially available for suppositories include PCCA Base MBK™ (Fatty Acid Base, PCCA), PCCA Base A™ (Polyglycol 1450 MW, NF, PCCA), PCCA Base F™ (Synthetic Cocoa Butter, PCCA), Wecobee® M, R, S, W (Vegetable Oil, Hydrogenated, tepan Company, Northfield, Ill.), Witepsol® H12, H15, W35 (Vegetable Oil, Hydrogenated), Hydrokote® M (Vegetable Oil, Hydrogenated, Abitec Corporation, Columbus, Ohio), COA Base (Fatty Acid Base, Spectrum Pharmacy Products, Tucson), Supposibase (PEG/Vegetable, Spectrum Pharmacy Products, Tucson), Base A, B, D, Polyethylene Glycols, Spectrum Pharmacy Products, Tucson), and Polybase (Polyethylene Glycol Blend, Gallipot, Inc., St. Paul, Minn.)

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, Science 249:1527-1533, 1990, which is incorporated herein by reference.

The inhibitors and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The pharmaceutical compositions of the invention contain an effective amount of an inhibitor and optionally therapeutic agents included in a pharmaceutically-acceptable carrier. The term pharmaceutically-acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The therapeutic agent(s), including specifically but not limited to the inhibitor, may be provided in particles. Particles as used herein means nano or microparticles (or in some instances larger) which can consist in whole or in part of the inhibitor or the other therapeutic agent(s) as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero order release, first order release, second order release, delayed release, sustained release, immediate release, and any combination thereof, etc. The particle may include, in addition to the therapeutic agent(s), any of those materials routinely used in the art of pharmacy and medicine, including, but not limited to, erodible, nonerodible, biodegradable, or nonbiodegradable material or combinations thereof The particles may be microcapsules which contain the inhibitor in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described by H. S. Sawhney, C. P. Pathak and J. A. Hubell in *Macromolecules*, (1993) 26:581-587, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly (isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant may be particularly suitable for treatment of chronic conditions. "Long-term" release, as used herein, means that the implant is constructed and arranged to deliver therapeutic levels of the active ingredient for at least 7 days, and preferably 30-60 days. Long-term sustained release implants are well-known to those of ordinary skill in the art and include some of the release systems described above.

The invention also includes kits. The kit has a container housing an R-type-VDCC inhibitor and optionally additional containers with other therapeutics such as anti-cerebral vasospasm drugs. The kit also includes instructions for administering the component(s) to a subject who has or is at risk of having a cerebral vasospasm.

In some aspects of the invention, the kit can include a pharmaceutical preparation vial, a pharmaceutical preparation diluent vial, and inhibitor. The vial containing the diluent for the pharmaceutical preparation is optional. The diluent vial contains a diluent such as physiological saline for diluting what could be a concentrated solution or lyophilized powder of inhibitor. The instructions can include instructions for mixing a particular amount of the diluent with a particular amount of the concentrated pharmaceutical preparation, whereby a final formulation for injection or infusion is prepared. The instructions may include instructions for use in a suppository or other device useful according to the invention. The instructions can include instructions for treating a patient with an effective amount of inhibitor. It also will be understood that the containers containing the preparations, whether the container is a bottle, a vial with a septum, an ampoule with a septum, an infusion bag, and the like, can contain indicia such as conventional markings which change color when the preparation has been autoclaved or otherwise sterilized.

Exemplary R-type VDCC inhibitors are described above. Other activity inhibitors or antagonists may be identified by those of skill in the art following the guidance described herein.

Libraries of compounds or other putative compounds can be screened to identify other activity inhibitors. Putative compounds can be synthesized from peptides or other biomolecules including but not limited to saccharides, fatty acids, sterols, isoprenoids, purines, pyrimidines, derivatives or structural analogs of the above, or combinations thereof and the like. Phage display libraries and chemical combinatorial libraries can be used to develop and select synthetic compounds which are capable of inhibiting R-type VDCC. Also envisioned in the invention is the use of compounds made from peptoids, random bio-oligomers (U.S. Pat. No. 5,650, 489), benzodiazepines, diversomeres such as dydantoins, benzodiazepines and dipeptides, nonpeptidal peptidomimetics with a beta-D-glucose scaffolding, oligocarbamates or peptidyl phosphonates.

Library technology can be used to identify small molecules, including small peptides, which bind to a R-type VDCC ligand binding site, or a protein interaction domain of an R-type VDCC. One advantage of using libraries for antagonist identification is the facile manipulation of millions of different putative candidates of small size in small reaction volumes (i.e., in synthesis and screening reactions). Another advantage of libraries is the ability to synthesize antagonists which might not otherwise be attainable using naturally occurring sources, particularly in the case of non-peptide moieties.

Many if not all of these compounds can be synthesized using recombinant or chemical libraries. A vast array of candidate compounds can be generated from libraries of synthetic or natural compounds. Libraries of natural compounds in the form of bacterial, fungal, plant and animal extracts are available or can readily produced. Natural and synthetically produced libraries and compounds can be readily modified through conventional chemical, physical, and biochemical means. In addition, compounds known to bind to and thereby act as antagonists of calcium channels may be subjected to directed or random chemical modifications such as acylation, alkylation, esterification, amidification, etc. to produce structural analogs which may function similarly or perhaps with greater specificity.

Small molecule combinatorial libraries may also be generated. A combinatorial library of small organic compounds is a collection of closely related analogs that differ from each other in one or more points of diversity and are synthesized by organic techniques using multi-step processes. As an example, analogs of SNX-482 can be generated which function as R-type VDCC inhibitors or antagonists. Analogs of these compounds can be synthesized using combinatorial libraries.

Combinatorial libraries include a vast number of small organic compounds. One type of combinatorial library is prepared by means of parallel synthesis methods to produce a compound array. A "compound array" as used herein is a collection of compounds identifiable by their spatial addresses in Cartesian coordinates and arranged such that each compound has a common molecular core and one or more variable structural diversity elements. The compounds in such a compound array are produced in parallel in separate reaction vessels, with each compound identified and tracked by its spatial address. Examples of parallel synthesis mixtures and parallel synthesis methods are provided in PCT published patent application W095/18972, published Jul. 13, 1995 and U.S. Pat. No. 5,712,171 granted Jan. 27, 1998 and its corresponding PCT published patent application W096/22529, which are hereby incorporated by reference.

The compounds generated using the recombinant and chemical libraries described herein can be initially screened to identify putative compounds by virtue of their ability to bind to R-type VDCC. Compounds such as library members can be screened for their ability to bind to R-type VDCC in vitro using standard binding assays well known to the ordinary artisan and described below. For binding to an R-type VDCC, the R-type VDCC may be presented in a number of ways including but not limited to cells expressing the R-type VDCC of interest, an isolated extracellular domain of an R-type VDCC, a fragment thereof or a fusion protein of the extracellular domain of an R-type VDCC and another protein such as an immunoglobulin or a GST polypeptide or in a purified (e.g., a recombinantly produced form). For some high throughput screening assays the use of purified forms of an R-type VDCC, its extracellular domain or a fusion of its extracellular domain with another protein may be preferable.

Isolation of binding partners may be performed in solution or in solid state according to well-known methods.

Standard binding assays are well known in the art, and a number of these are suitable in the present invention including ELISA, competition binding assay, sandwich assays, radioreceptor assays using radioactively labeled ligands or substrates of R-type VDCC (with the binding of the native, radioactively labeled, activator being competed with by the putative antagonist), electrophoretic mobility shift assays, immunoassays, cell-based assays such as two- or three-hybrid screens, etc. The nature of the assay is not essential provided it is sufficiently sensitive to detect binding of a small number of library members.

A variety of other reagents also can be included in the binding mixture. These include reagents such as salts, buffers, neutral proteins (e.g., albumin), detergents, etc. which may be used to facilitate optimal molecular interactions. Such a reagent may also reduce non-specific or background interactions of the reaction components. Other reagents that improve the efficiency of the assay may also be used. The mixture of the foregoing assay materials is incubated under conditions under which the R-type VDCC normally specifically binds one or more of its activators. The order of addition of components, incubation temperature, time of incubation, and other parameters of the assay may be readily determined. Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 0.1 and 10 hours. After incubation, the presence or absence of specific binding between the compounds is detected by any convenient method available to the user.

Typically, a plurality of assay mixtures are run in parallel with different agent concentrations to obtain a different response to the various concentrations. One of these concentrations serves as a negative control, i.e., at zero concentration of agent or at a concentration of agent below the limits of assay detection.

Once compounds have been identified which are capable of interacting with R-type VDCC these compounds can be further screened for their ability to modulate vasoconstriction. An exemplary assay for measuring the effect of a compound on vasoconstriction, the patch clamp technique, is described in the Examples. In that assay, vascular smooth muscle cells are removed from SAH rabbits and bathed in a physiological solution and then subjected to the patch clamp technique. The identical arterial segments may be used to test the contractile response to a control substance and the test compound (e.g., compounds which are identified as described above). Contractile responses can be measured directly using the methods described in the examples. The muscle cells may be exposed to increasing amounts of the test compound in order to arrive at a dose-response curve and an estimation of the appropriate dosage. Modulation of vasoconstriction can also be measured using an assay which records intraluminal pressure in perfused isolated vessels.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Methods

SAH Model. New Zealand white rabbits (males, 3.0-3.5 kg) were initially anesthetized by isoflurane (5%) using an induction chamber, then intubated and maintained on isoflurane (2-3%) for the duration of the surgical procedure. As described previously (Ishiguro M, et al *Am J Physiol Heart Circ Physiol*. 2002; 283:H2217-H2225), 3 ml of unheparinized blood was injected into the cisternal magna. Buprenorphine (0.01 mg/kg) was given every 12 hours (for 36 hours, then as needed) as an analgesic. In the present study, cerebral arteries were obtained from control (no surgery) and SAH (5 days post-surgery) animals. Rabbits were euthanized by exsanguination under deep pentobarbital anesthesia (i.v.; 60 mg/kg body weight). Posterior cerebral and cerebellar arteries (100-200 µm diameter), which are consistently located within the clot region of SAH animals, were dissected from the brain in cold (4° C.), oxygenated (20% $O_2$/5% $CO_2$/75% $N_2$) physiological saline solution (PSS) of the following composition (in mmol/L): 119 NaCl, 4.7 KCl, 24 $NaHCO_3$, 1.2 $KH_2PO_4$, 1.6 $CaCl_2$, 1.2 $MgSO_4$, 0.023 EDTA, 10 glucose. All protocols were conducted in accordance with the guidelines for the care and use of laboratory animals (NIH publication 85-23, 1985) and followed protocols approved by the Institutional Animal Use and Care Committee of the University of Vermont, USA.

Diameter Measurements in Isolated Arteries. Cerebral artery segments were cannulated on glass pipettes mounted in a 5 ml myograph chamber (Living Systems Instruments, Burlington, Vt.) and superfused with aerated PSS (20% $O_2$/5% $CO_2$/75% $N_2$) at 37° C. and pH 7.4, as previously described (Ishiguro M, et al *Am J Physiol Heart Circ Physiol*. 2002; 283:H2217-H2225). Arterial diameter was measured with video edge detection equipment and recorded using data acquisition software (Dataq Instruments Inc., Akron, Ohio).

Organ culture of cerebral arteries. Cerebral arteries (100 to 200 µm in diameter) were isolated from the freshly harvested anterior and posterior circulation and maintained in cold MOPS solution. Once blood was gently flushed from the lumen, arteries were transferred into serum free Dulbecco's modified Eagle's medium (DMEM)/F12 supplemented with penicillin-streptomycin (1% vol/vol) and placed in an incubator at 37° C. with 5% $CO_2$ and 97% humidity. Arteries were cultured for 0-5 days in the presence or absence of purified hemoglobin $A_O$ (oxy form; 10 µmol/L, Hemosol; Toronto, Canada). Culture medium was changed twice daily to maintain oxyhemoglobin levels.

Measurements of VDCC currents. Vascular smooth muscle cells were enzymatically isolated from cerebral arteries as previously described (Wellman G C et al. *Stroke*. 2002; 33:802-808). The conventional whole cell configuration of the patch clamp technique was used to measure whole cell VDCC currents in cerebral artery myocytes. The external (bath) solution contained (in mmol/L): 125 NaCl, 10 $BaCl_2$, 5 KCl, 10 HEPES, 1 $MgCl_2$, 10 glucose, pH adjusted to 7.4 with NaOH. Patch pipettes (3-5 MΩ) were filled with an internal solution that contained (in mmol/L): 130 CsCl, 10 ethylene glycol-bis(β-aminoethyl ether)-N,N,N',N'-tetraacetic acid, 10 HEPES, 1 $MgCl_2$, 2 ATP, 0.5 GTP, 5 phosphocreatine, 10 glucose, pH adjusted to 7.2 with CsOH. $K_i$ values for diltiazem and nifedipine were determined from Hill plot of concentration-response curves of currents using the following equation: $y = I_{max}/\{1+([drug]/K_i)^n\}+r$, where $I_{max}$, [drug], n and r denote the maximum effect, concentration of drug (diltiazem or nifedipine), Hill coefficient and drug resistant current, respectively. Experiments were performed at 24-26° C.

RNA isolation and RT-PCR. Total RNA was extracted and quantified from cultured arteries at Day 5 or freshly harvested cerebral arteries and first strand cDNA was synthesized using Omniscript® RT kit (Qiagen, Valencia, Calif.). To perform RT-PCR, $\alpha_1$ VDCC subunit specific primers were generated from unique coding regions for $Ca_v$ 2.3 and $Ca_v$ 1.2. The following sets of primers were used: $Ca_v$ 2.3 (GenBank Accession no. X67855) sense nucleotides 5692-5709 (5'-CCC CAG GAA ATC ATC GCC-3' (SEQ ID NO:1)), and antisense nucleotides 6771-6750 (5'-GTC CTC AGT GCT ACT CAG C-3' (SEQ ID NO:2)); $Ca_v$ 1.2 (GenBank Accession no. X55763) sense nucleotides 5380-5398 (5'-AAT GCC AAC AAC ACT GCC C-3'(SEQ ID NO:3)), antisense nucleotides 6211-6193 (5'-CTT CGG AAA TCA AGA CCG C-3' (SEQ ID NO:4)). For the experiments on oxyhemoglobin exposed arteries a different primer set was used for CaV2.3 (GenBank Accession #X67855): sense nucleotides 6562-6580 (5'-GAG CAG CGA CAA CAC CTA C-3' (SEQ ID NO:8)) and antisense nucleotides 6996-6978 (5'-GCT GGT GGA GAG AAG TTG C-3' (SEQ ID NO:9)). cDNA was amplified under the following RT-PCR conditions: 94° C. 3 min for pre-incubation, 94° C. 1 min, 55-57° C. 1 min, 72° C. 1.5 min for 35 cycles followed by an incubation at 72° C. for 10 min. Nested PCR was employed using another unique coding region of CaV2.3 with the following sets of primers: sense nucleotides 3586-3605 (5'-ACC CCT CGT CCT GTC CTC AC-3' (SEQ ID NO:10)) and antisense nucleotides 3773-3754 (5'-TGC TCT CGG TGG TGA CCT TG-3' (SEQ ID NO:11)) for the 1$^{st}$ round PCR; sense nucleotides 3607-3625 (5'-CGA GGG TGT GGG GAA AGA G-3' (SEQ ID NO:12)) and antisense nucleotides 3767-3748 (5'-CGG TGG TGA CCT TGT CTG TG-3' (SEQ ID NO:13) for the 2$^{nd}$ round PCR.

Immunofluorescence. Whole-mount arteries were fixed with 10% formalin at room temperature for 1.5 hours then permeabilized and blocked with 0.1% Triton-X 100/2% bovine serum albumin in PBS (pH 7.4). Arteries were stained using rabbit anti-$Ca_v$ 2.3 (primary antibody obtained from Alomone labs, Jerusalem, Israel) and Cy5 anti-rabbit as a secondary antibody. Images were obtained using a Bio-Rad laser confocal microscope (excitation 650 nm and emission 670 for Cy5) (Bio-Rad Laboratories, Hercules, Calif.). The cyanine nuclear dye, YOYO®-1 (excitation 490 nm and emission 510 nm) was used to identify cell nuclei (Molecular Probes, Inc., Eugene, Oreg.).

Statistical Analysis. Data are presented as mean±SEM. Statistical significance was considered at the level of $p<0.05$ (*) or $p<0.01$ (**) using Student's t-test.

Example 1

Figure 1B:
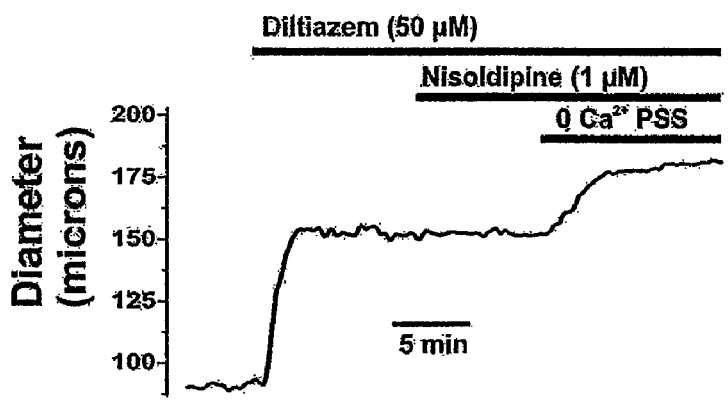
Figure 1C:
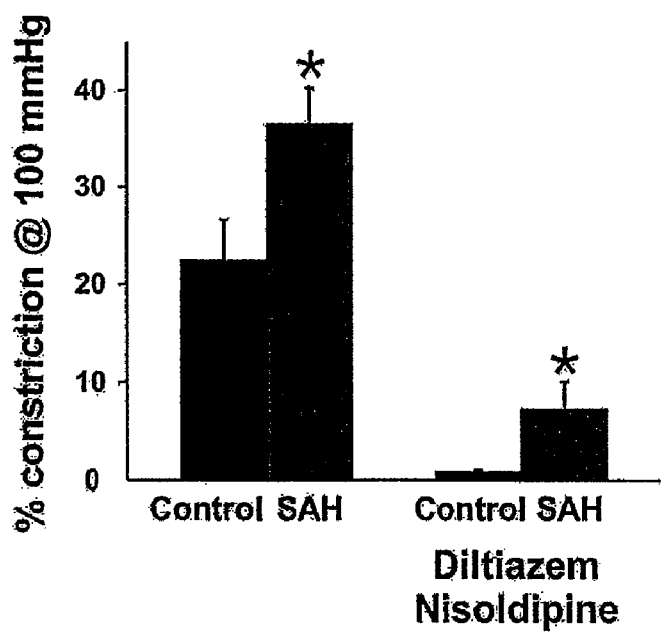
FIG. 1C is a graph showing a summary of pressure-induced constriction of cerebral arteries from control and SAH rabbits. The y-axis shows % constriction after pressurization. The gray bars represent SAH rabbits and the black bars represent control rabbits. The x-axis shows measurements with and without L-type VDCC antagonist. Constriction is expressed as a percent decrease of the fully dilated diameter. *$p<0.05$.

Cerebral Artery Constriction Becomes Partially Resistant to L-Type VDCC Antagonists Following SAH To examine the effects of subarachnoid blood on small diameter cerebral arteries, an established model of SAH was used, where blood (3 ml) was injected into the cisterna magna of anesthetized rabbits (Ishiguro M, et al *Am J Physiol Heart Circ Physiol*. 2002; 283:H2217-H2225). Five days following this surgery, to obtain in vitro diameter measurements using video microscopy, isolated 100-200 µm diameter cerebral arteries were cannulated and pressurized to 100 mm Hg in vitro. While arteries from both control and SAH animals constricted to increased intravascular pressure, there were significant differences in the characteristics of these pressure-induced responses between groups. Notably, pressure-induced constriction was approximately twice as great in arteries from SAH animals (FIG. 1). In addition, there was a fundamental difference in how these small diameter arteries from SAH animals responded to L-type VDCC antagonists (inhibitors). In arteries from control animals, pressure-induced constriction at 100 mmHg was abolished by diltiazem (50 µmol/L), an L-type VDCC antagonist (FIG. 1A). However, in marked contrast to arteries from healthy animals, pressure-induced constriction of cerebral arteries from SAH animals was partially resistant to a combination of diltiazem (50 µmol/L) and nisoldipine (1 µmol/L). In arteries from SAH animals, the constriction resistant to L-type VDCC antagonists, representing approximately 20% of the total constriction, was reversed by removal of extracellular $Ca^{2+}$ from the physiological saline solution (0 $Ca^{2+}$ PSS) (FIG. 1B and FIG. 1C). These data suggest an additional $Ca^{2+}$ entry pathway resistant to antagonists of L-type VDCCs emerges in cerebral arteries following SAH and contributes to enhanced pressure-induced constriction.

Example 2

Enhanced VDCC Currents with Distinct Biophysical Properties Following SAH

Figure 2C:
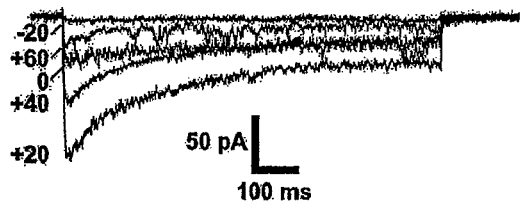
FIG. 2C is a graph showing the summary of current-voltage relationship of membrane currents in cells isolated from control (n=13) and SAH (n=11) myocytes. *$p<0.05$ **$p<0.1$. The y-axis represents current density in (pA/pf) and the x-axis represents membrane potential in milliamps.
Figure 2C:
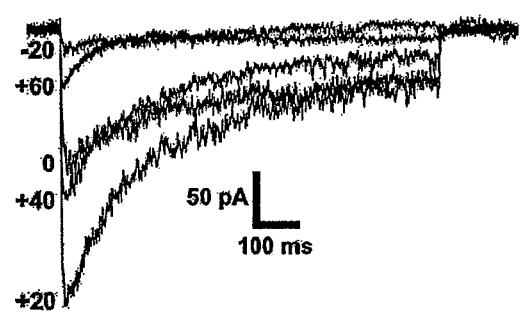
Figure 2C:
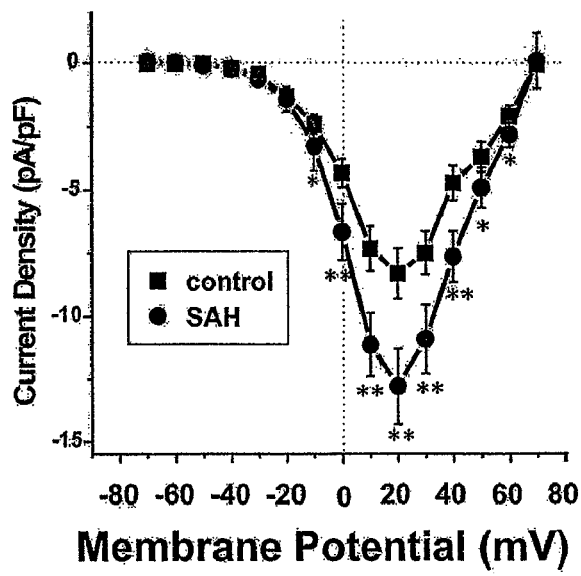
Figure 2D:
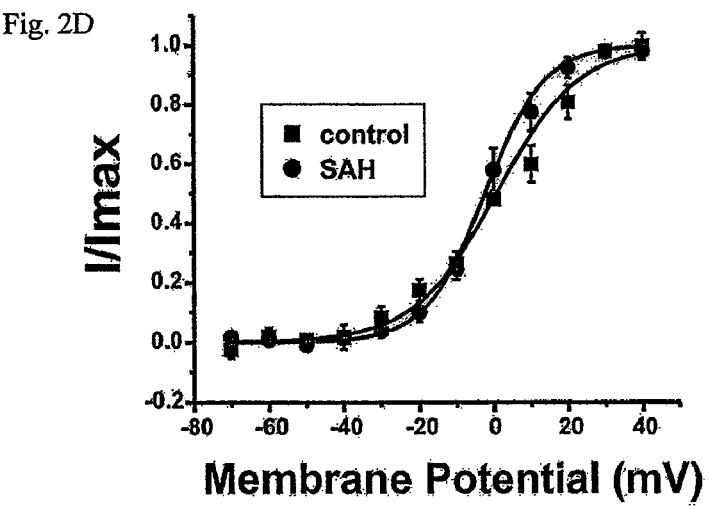
FIG. 2D is a graph showing tail currents expressed as a ratio of the maximum current for each cell (I/Imax). Tail currents were obtained by stepping cells to membrane potential between −70 mV and +40 mV for 20 ms, then measuring inward current at −80 mV. The interval between voltage steps was 20 s. The voltage for half-maximal ($V_{0.5, act}$) activation was obtained from Boltzmann fit of tail currents. $V_{0.5,act}$ for control (0.8±0.7 mV, n=4) and SAH (−2.3±0.6 mV, n=7) were not significantly different, $p>0.05$.
Figure 3A:
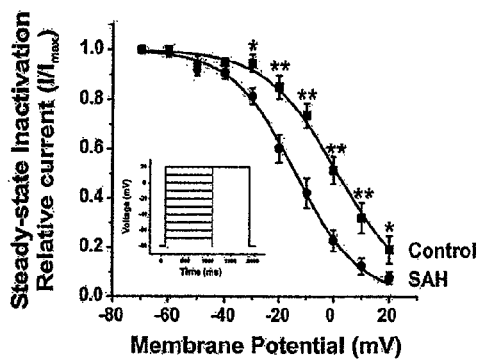
FIG. 3A shows steady state inactivation of VDCC currents from control and SAH myocytes were obtained using a double-step voltage protocol (see inset of FIG. 3A) where every 10 seconds, cells are stepped from −80 mV to a membrane potential between −70 and +20 mV for 1 s, before membrane current is determined at +20 mV. The voltage for half-maximal ($V_{0.5,inact}$) inactivation for control (1.4±1.6 mV, n=6) and SAH (−13.8±1.2 mV, n=10) cells were determined from Boltzmann fit of data. The y-axis is the ratio of maximum current for each cell (I/Imax).
Figure 3B:
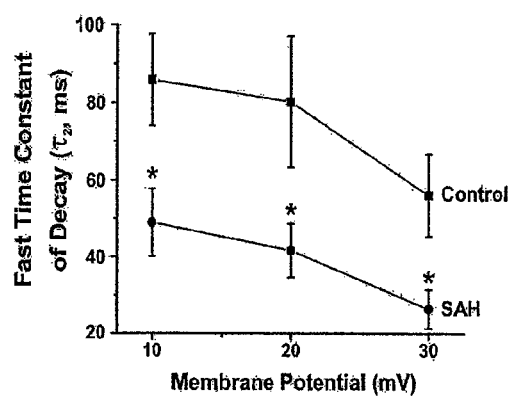
FIG. 3B is a summary of fast inactivation time constants from control (n=10) and SAH (n=10) myocytes. Fast inactivation time constants ($\tau_1$) were obtained by double exponential fit of current decay ($I=A_1 e^{-x/\tau_1}+A_2 e^{-x/\tau_2}+C$) during a 800 ms voltage step from −80 mV to +20 mV.
Figure 3C:
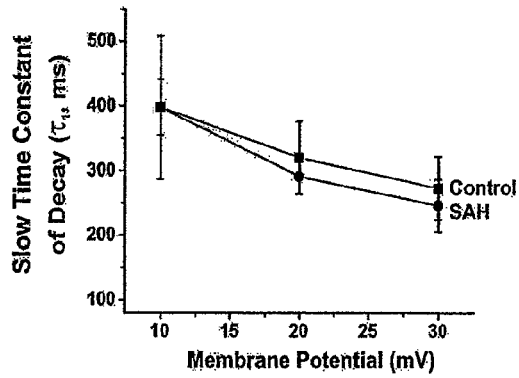
FIG. 3C is a summary of slow inactivation time constants ($\tau_2$) from control (n=10) and SAH (n=10) myocytes. For figures C and D the y-axis is time in milliseconds and the x-axis is membrane potential in millivolts.
Figure 3D:
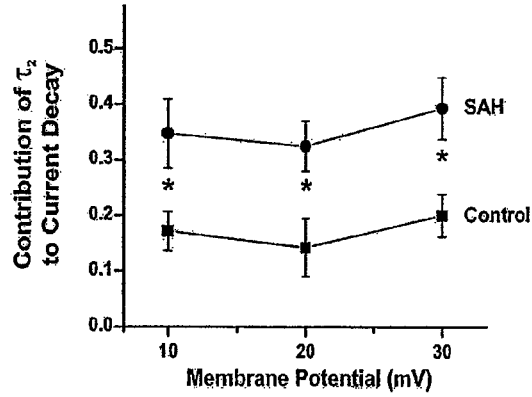
FIG. 3D shows the contribution of fast time constant to current decay ($A_1/A_1+A_2+C$). Fitting parameters at +20 mV were: $A_1$=−52.5 pA (control) and −83.0 pA (SAH), $A_2$=−15.5 pA (control) and −59.1 pA (SAH), C=−27.8 pA (control) and −44.1 pA (SAH). *$p<0.05$, **$p<0.01$. The y-axis represents the time constant and the x-axis is membrane potential in millivolts.

To further explore the contribution of VDCCs to enhanced cerebral artery constriction following SAH, conventional whole-cell patch clamp electrophysiology was performed on freshly isolated cerebral artery myocytes. No gross morphological distinctions were apparent between myocytes from control and SAH animals. Cell capacitance, an index of cell membrane surface area, was similar between the two groups (control: 12.6±0.3 pF, n=252; SAH: 12.9±0.3 pF, n=315). Using 10 mmol/L $Ba^{2+}$ as a charge carrier, depolarizing voltage steps from a holding potential of −80 mV elicited greater inward membrane currents in myocytes isolated from SAH animals (FIG. 2A and FIG. 2B). Membrane currents from both control and SAH myocytes exhibited a "V-shaped" current-voltage relationship, with peak current at +20 mV (FIG. 2C). Current density at +20 mV was markedly enhanced (≈50%) in myocytes from SAH (−12.8±1.5 pA/pF) versus control (−8.3±1.3 pA/pF) animals. The voltage for half-maximal activation ($V_{0.5,act}$) obtained from Boltzmann fit of tail currents was similar between myocytes isolated from control animals (0.8±0.7 mV) and SAH animals (−2.3±0.6 mV), consistent with the activation of high voltage-activated channels, but not low voltage-activated channels, in both cell types (FIG. 2D). To determine whether enhanced VDCC currents in cerebral artery myocytes from SAH animals had inactivation properties distinct from the L-type VDCCs in myocytes of control animals, VDCC currents were measured in isolated monocytes from each group. The voltage for half-maximal steady-state inactivation ($V_{0.5,inact}$) was shifted by about −15 mV in SAH myocytes (FIG. 3A). In addition, membrane currents from SAH myocytes exhibited a more rapid inactivation. Membrane current decay from myocytes of both control and SAH animals were best fit to a double exponential decay. Time constants for fast inactivation ($\tau_1$) were decreased by 40-50% at voltages between +10 mV and +30 mV in SAH compared to control myocytes (FIG. 3B). Time constants for slow inactivation ($\tau_2$) were not significantly different between groups (FIG. 3C). Further, $\tau_1$ made a greater contribution to current decay in cerebral artery myocytes isolated from SAH compared to control animals (FIG. 3D). These data demonstrated a fundamental change in the properties of VDCC currents, suggesting the possibility that a second, more rapidly inactivating, high voltage-activated $Ca^{2+}$ channel (e.g. R-type) contributed to enhanced VDCC currents in cerebral artery myocytes following SAH.

Example 3

Figure 4A:
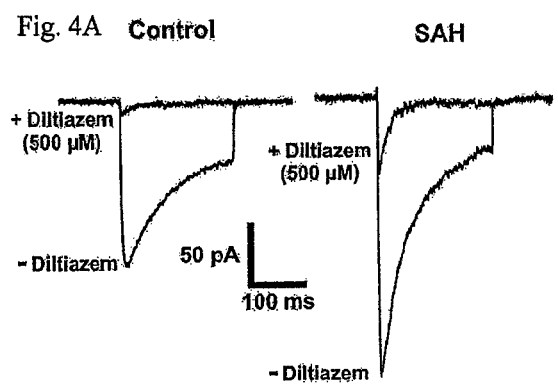
FIG. 4A shows current recordings during voltage steps from −80 mV to +20 mV in the presence and absence of diltiazem (500 μmol/L).
Figure 4B:
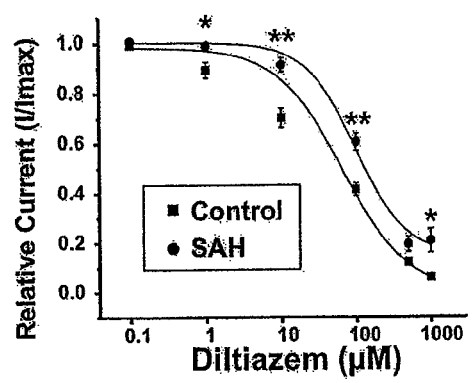
FIG. 4B shows concentration response curves of current inhibition by diltiazem in control (n=6-15 cells) and SAH (n=4-20 cells) myocytes. The y-axis is I/Imax and the x-axis is concentration of diltiazem in micromoles.
Figure 4C:
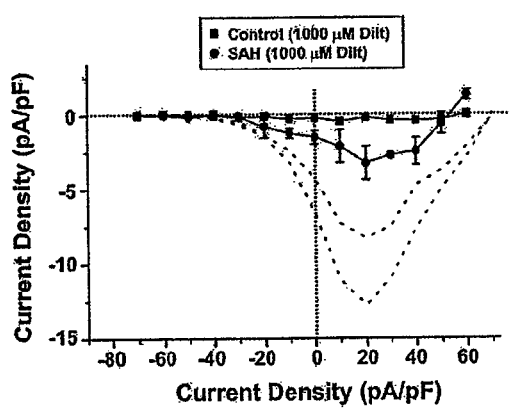
FIG. 4C shows the summary of current-voltage relationship of membrane currents in cells isolated from control (■) and SAH (●) myocytes in the presence of 1000 μmol/L diltiazem. Dashed lines represent the current-voltage of control (black dashed line) and SAH (gray dashed line) in the absence of diltiazem (from FIG. 2C).
Figure 4D:
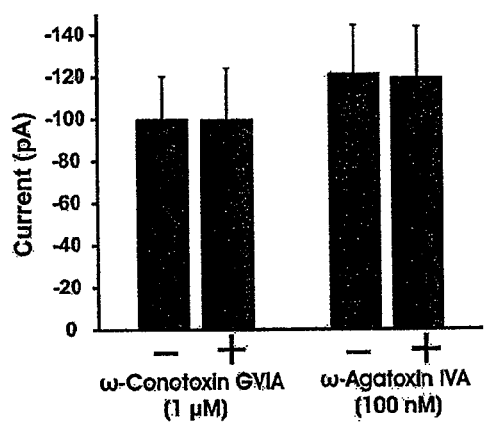
FIG. 4D shows the summary of the effects of ω-conotoxin GVIA (1 μmol/L, n=4) and ω-agatoxin IVA (100 nmol/L, n=4) on VDCC currents from SAH myocytes. *p<0.05, **p<0.01. The y-axis is current in milliamps and the x-axis is presence or absence of drug.
Figure 5A:
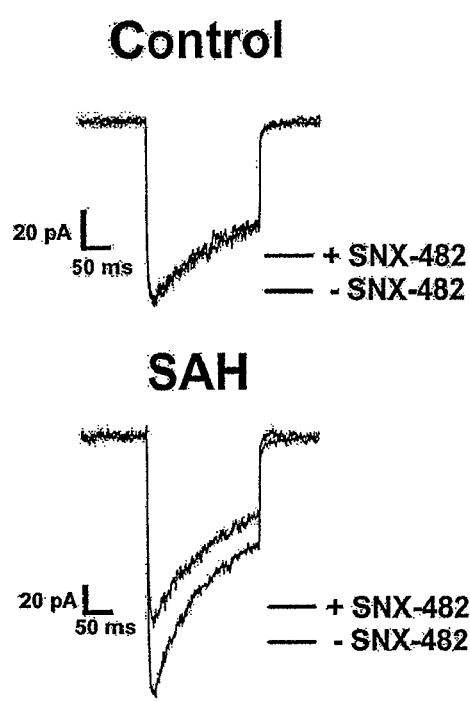
FIG. 5A shows current recordings during voltage steps from −80 mV to +20 mV in the presence (gray line) and absence (black line) of SNX-482 (200 nmol/L) obtained from cerebral artery myocytes of control (upper) and SAH (lower) animals.
Figure 5B:
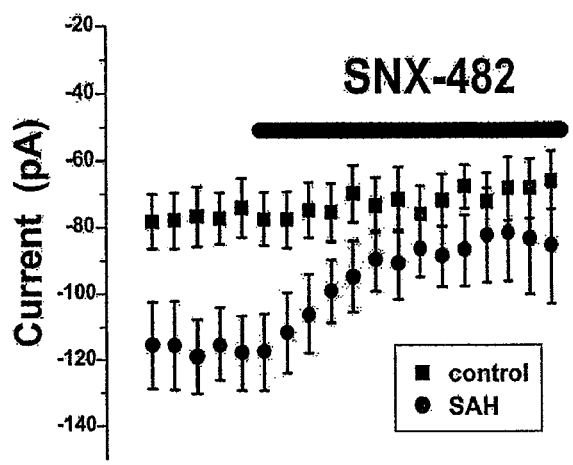
FIG. 5B shows averaged peak current from voltage steps from −80 to +20 mV obtained at 20 s intervals of control (■) and SAH (●) animals. Solid bar represents the addition of SNX-482 to the extracellular solution. The y-axis is current in picoamps.
Figure 5C:
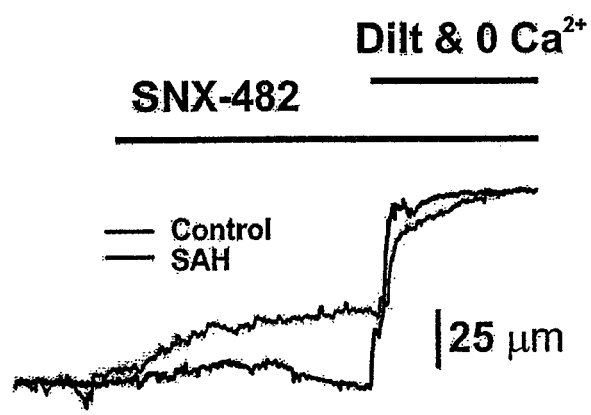
FIG. 5C shows diameter recordings obtained from isolated cerebral arteries pressurized to 100 mmHg. Diltiazem (50 μmol/L) in nominally $Ca^{2+}$-free physiological saline solution (PSS) (0 $Ca^{2+}$ PSS) was used to obtain maximal dilation for each artery. Control animals are represented by the gray line and SAH animals are represented by the black line.
Figure 5D:
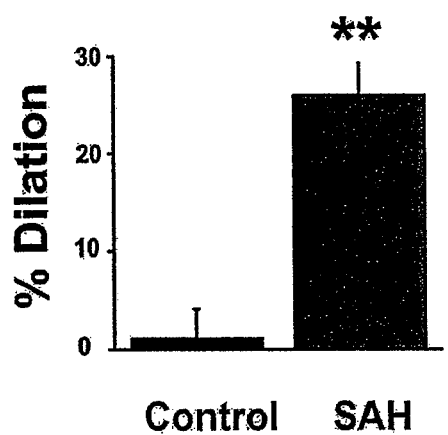
FIG. 5D shows the summary of effects of SNX-482 on isolated cerebral arteries obtained from control and SAH animals. **p<0.01. The y-axis is percent dilation.

SNX-482-Sensitive VDCC Currents Emerge in Cerebral Artery Myocytes Following SAH To examine whether pharmacological agents that specifically block various VDCC subtypes differentially impact currents from control and SAH myocytes, membrane potential was measured in the presence and absence of drug compound. Consistent with the functional data shown in FIG. 1, the L-type VDCC antagonist diltiazem was a less effective inhibitor of membrane currents in cerebral artery myocytes isolated from SAH animals. While the highest concentration of diltiazem (1000 µmol/L) used in this study completely blocked currents from control myocytes, approximately 20% of the current in SAH myocytes was resistant to this L-type VDCC antagonist (FIGS. 4A and 4B). The current-voltage relationship of the diltiazem-resistant current was consistent with high voltage-activated VDCCs and similar to membrane currents from control and SAH animals in the absence of diltiazem (FIG. 4C). The diltiazem-resistant component of VDCC currents present in SAH myocytes exhibited rapid inactivation kinetics ($\tau_1$=10.5±1.0 ms at +20 mV, n=10). Excluding the diltiazem-resistant component, VDCC currents from SAH myocytes were also less sensitive to diltiazem ($K_i$=99.5±10.4 µmol/L) compared to control ($K_i$=41.4±5.7 µmol/L) myocytes. In a similar manner (i.e. excluding the resistant component), SAH myocytes exhibited decreased sensitivity to the dihydropyridine L-type $Ca^{2+}$ channel antagonist, nifedipine (SAH: $K_i$=125.8±6.4 nmol/L versus control: $K_i$=55.6±3.9 nmol/L). VDCC currents resistant to high concentrations of nifedipine (10 µmol/L) in SAH myocytes were abolished by cadmium (200 µmol/L), a non-selective $Ca^{2+}$ channel antagonist (n=4, data not shown). The selective antagonist of N-type $Ca^{2+}$ channels, ω-Conotoxin GVIA (McCleskey E W, et al *Proc Natl Acad Sci USA*. 1987; 84:4327-4331) (1 µmol/L) and P/Q type $Ca^{2+}$ channel antagonist, ω-Agatoxin IVA (Mintz I M, et al *Nature*. 1992; 355:827-829.) (100 nmol/L) did not alter peak inward currents at +20 mV in SAH myocytes (FIG. 4D). While antagonists of N- and P/Q-type channels were without effect, the R-type $Ca^{2+}$ channel antagonist, SNX-482 (200 nmol/L) (Newcomb R, et al. *Biochemistry*. 1998; 37:15353-15362), reduced VDCC currents by approximately 30% in myocytes from SAH, but had no effect on VDCC currents in myocytes from control animals (FIGS. 5A and 5B). Consistent with these electrophysiological data, SNX-482 dilated pressurized cerebral arteries from SAH animals by approximately 30%, but had no significant effect on pressurized arteries from controls (FIGS. 5C and 5D). These data suggest that the enhanced VDCC currents observed in cerebral artery myocytes following SAH represent the expression of R-type $Ca^{2+}$ channels.

Example 4

R-Type ($Ca_v2.3$) VDCC Expression in Cerebral Artery Myocytes Following SAH

Figure 6A:
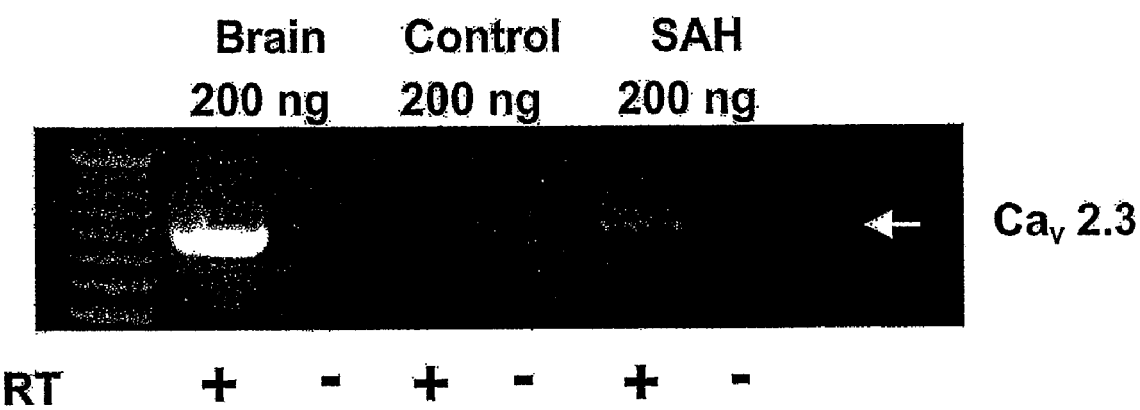
FIG. 6A shows RT-PCR performed using primers specific for $Ca_v$ 2.3. The expected 1.1 kb product (white arrow) was detected using 200 ng of total RNA extracted from cerebral arteries from SAH, but not in control animals. $Ca_v$ 2.3 was also detected in RNA isolated from brain. PCR reactions were performed with (+) and without (−) reverse transcriptase (RT).
Figure 6B:
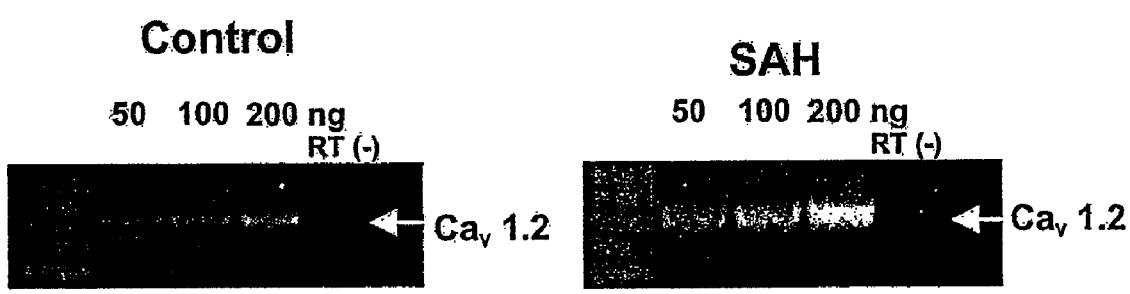
FIG. 6B shows RT-PCR performed on 50, 100 and 200 ng of RNA extracted from intact cerebral arteries of control (left) and SAH (right) animals. Using primers specific for the L-type VDCC ($Ca_v$ 1.2) the expected product (white arrow) was detected in cerebral arteries from both SAH and control animals. PCR reactions were performed with (+) and without (−) reverse transcriptase (RT) on 200 ng samples.
Figure 7A:
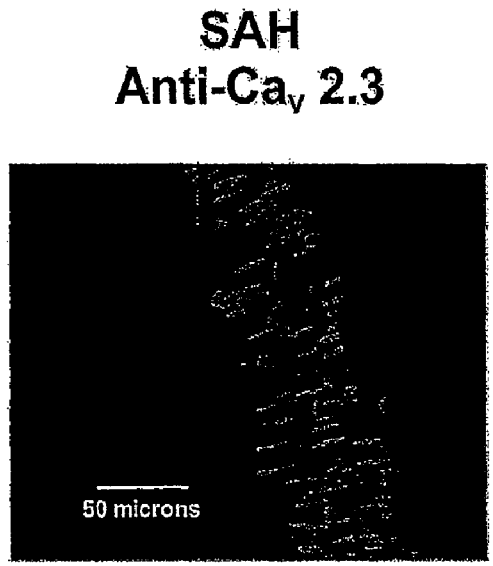
FIGS. 7A and 7B show staining, in blue, of a cerebral artery from a SAH (FIG. 7A) and a control (FIG. 7B) animal using an anti-$Ca_v$ 2.3 primary antibody and a Cy5 anti-rabbit secondary antibody. The cyanine nuclear dye, YOYO®-1 was used to identify cell nuclei (in green).
Figure 7B:
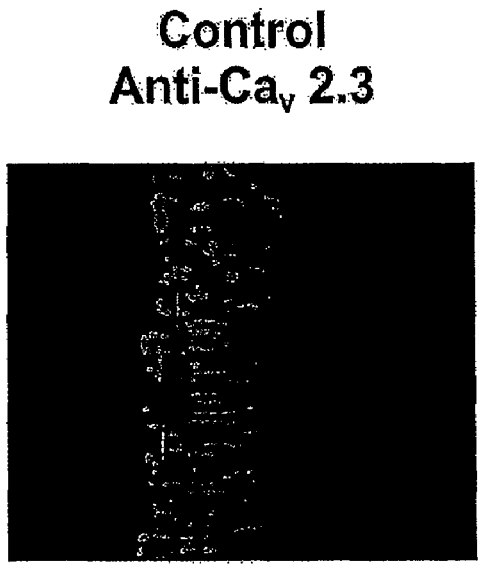
Figure 7C:
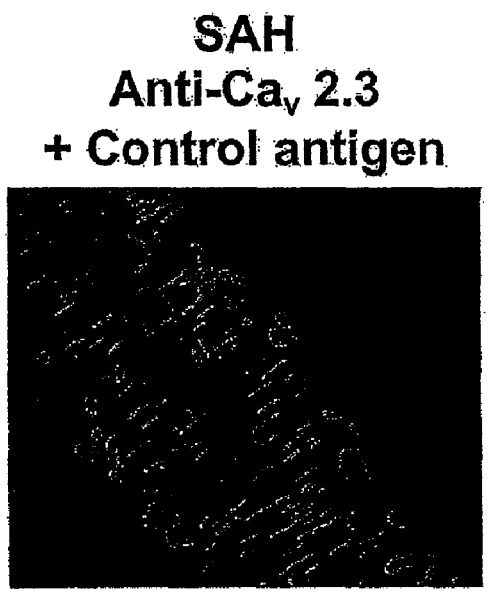
FIG. 7C is an image of an artery from a SAH animal when the anti-CaV 2.3 antibody was preadsorbed with the control antigen peptide.
Figure 7D:
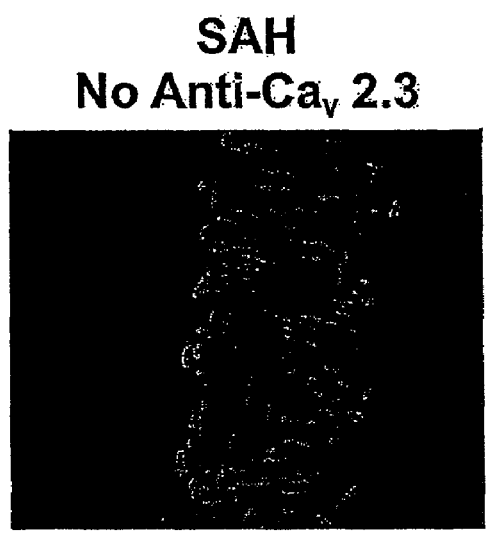
FIG. 7D is an image of an artery from an SAH animal when the anti-$Ca_v$ 2.3 antibody was omitted from the staining procedure. Images were obtained using the same laser intensity and the scale bar in panel A is applicable to all panels.

RT-PCR was performed to examine whether mRNA of the pore-forming $\alpha_1$ subunit of the R-type VDCC ($\alpha_{1E}$ encoded by the gene $Ca_V 2.3$) was present in cerebral artery myocytes following SAH. Using $\alpha_{1E}$-specific primers generated from rabbit $Ca_V 2.3$ (see methods for sequence), the expected 1.1 kb RT-PCR product of these primers was detected in cerebral arteries obtained from SAH animals, but not control animals (n=4) (FIG. 6A). DNA sequencing verified that the product generated matched the expected sequence of $Ca_V$ 2.3. No product was detected in reactions performed in the absence of reverse transcriptase consistent with the absence of genomic DNA contamination of the RNA samples. However, the pore-forming $\alpha_1$ subunit of the L-type VDCC ($\alpha_{1C}$ encoded by the gene $Ca_V$ 1.2) was detected in both the control and SAH mRNA samples that were also used to examine $Ca_V$ 2.3 expression (FIG. 6B). RT-PCR did not detect $Ca_V$ 2.3 mRNA in larger diameter basilar arteries obtained from control or SAH animals.

Using confocal microscopy and the nuclear dye, YoYo®, to identify vascular smooth muscle cells, a much greater immunofluorescent labeling of $Ca_V$ 2.3 was detected in the smooth muscle of arteries from SAH, compared to control animals (FIG. 7). The enhanced fluorescence in arteries from SAH animals was abolished by either preadsorption of the primary ($Ca_V$ 2.3) antibody with a specific blocking peptide or exclusion of the $Ca_V$ 2.3 antibody from the staining protocol (labeling with secondary antibody only).

These qualitative data provide the first evidence for R-type VDCC expression in small diameter cerebral arteries. Further, these data suggest that expression of pore-forming VDCC $\alpha_1$ subunits is altered in cerebral artery myocytes following subarachnoid hemorrhage with expression of only $Ca_V$ 1.2 in control animals, but with expression of both $Ca_V$ 1.2 and $Ca_V$ 2.3 following subarachnoid hemorrhage.

Example 5

Oxyhemoglobin Reduces the Ability of Diltiazem to Dilate Cerebral Arteries

Figure 8A:
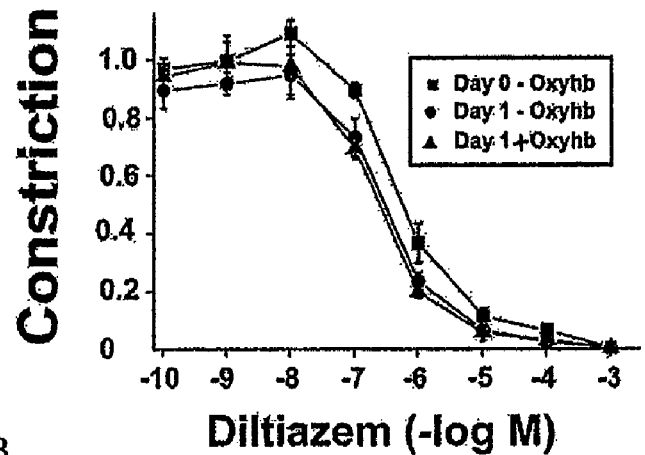
FIG. 8A shows the profile of the control sample directly upon harvest (day 0; square) and at day 1 (circle). The day 1 oxyhemoglobin treated sample is depicted by triangles.
Figure 8B:
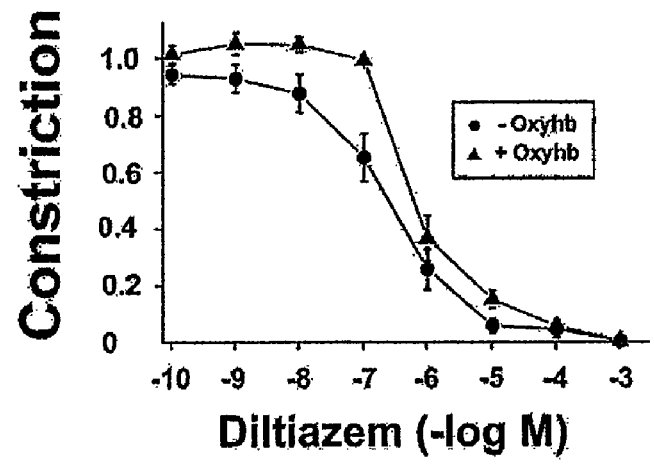
FIG. 8B and FIG. 8C show the treatment regimens at 3 and 5 days respectively, with the untreated samples depicted by circles and the treated samples depicted by triangles. Experimental values are the average of four to seven experiment. Error bars represent the standard error of the mean.
Figure 8C:
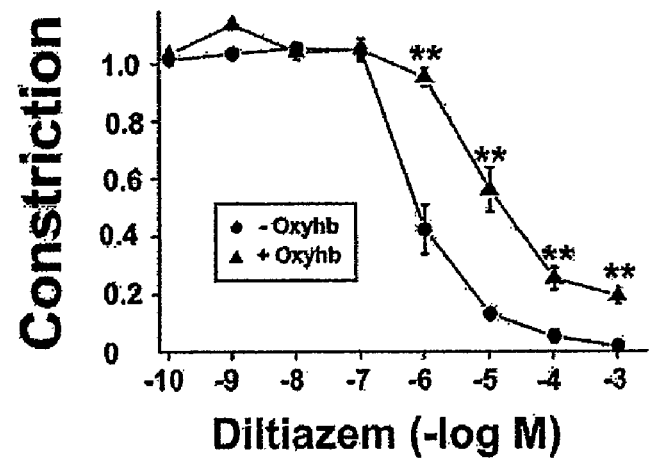

The impact of 1-5 day oxyhemoglobin exposure on $K^+$-induced constrictions and L-type VDCC function in small diameter cerebral arteries was examined. In freshly isolated arteries, increasing the concentration of extracellular $K^+$ to 60 mmol/L caused a constriction of 97±28 µm, representing 67±5.6% decrease in diameter (n=4). Diltiazem caused a concentration-dependent reversal of the $K^+$-induced constrictions. In freshly isolated arteries, 1 mmol/L diltiazem reduced $K^+$-induced constriction by 99.7±0.4 percent. Diltiazem at the same concentration caused a similar reversal of $K^+$-induced constrictions in cerebral arteries organ cultured for a period of one or three days regardless of whether 10 µmol/L oxyhemoglobin was included in the media (FIGS. 8A, B). Under each of these conditions, diltiazem caused a complete reversal of $K^+$-induced constrictions with an $IC_{50}$ value of diltiazem for vasodilation of approximately 1 µmol/L (Table 1). After 5 days of organ culture, a marked difference emerged between arteries maintained in the presence and absence of oxyhemoglobin. In the absence of oxyhemoglobin, diltiazem completely reversed $K^+$-induced constrictions in a manner similar to arteries that were either freshly isolated or organ cultured for 1-3 days. However, with arteries organ cultured with oxyhemoglobin for 5 days, $K^+$-induced constrictions less sensitive to diltiazem as evidenced by a 10-fold increase in the $IC_{50}$ value (16.9±6.9 µmol/L). In addition, these arteries became partially resistant to diltiazem; approximately 20% of the $K^+$-induced constrictions could not be reversed by the drug even at 1 mmol/L, which is almost 1000 fold higher concentration of $IC_{50}$ for freshly isolated or 1-3 days cultured arteries (FIG. 8C). These data suggest another mechanism, in addition to L-type VDCC, contributes to $K^+$-induced constrictions of arteries exposed to oxyhemoglobin for 5 days.

TABLE 1

$EC_{50}$ values of diltiazem treatment of $K^+$ induced constricted arteries at various time points. Both control and oxyhemoglobin treated samples are tabulated.

| | Day 0 | Day 1 | Day 3 | Day 5 |
|---|---|---|---|---|
| −Oxy Hb | 1.02 ± 0.07 | 0.76 ± 0.07 | 0.78 ± 0.12 | 1.1 ± 0.10 |
| +Oxy Hb | | 0.95 ± 0.14 | 1.07 ± 0.06 | 16.9 ± 6.9 |

Example 6

R-Type VDCC Blocker SNX-482 Dilates Cerebral Arteries Exposed to Oxyhemoglobin

Figure 9:
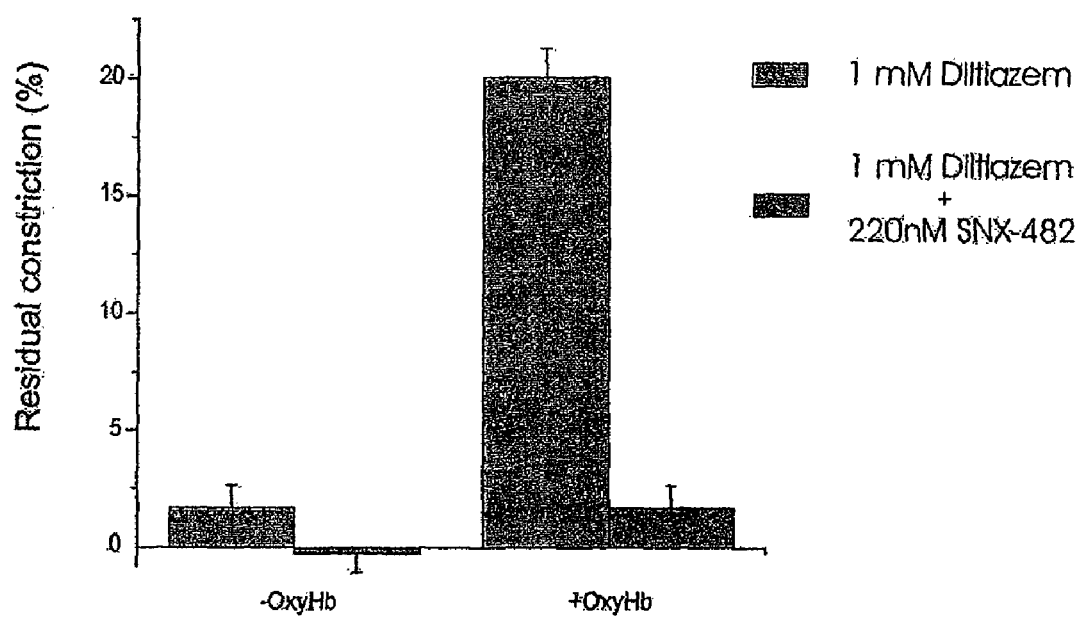
FIG. 9 shows the percentage of residual constriction of the arteries that have been cultured for 5 days under different treatment regimens. The left hand side of the panel shows control treatment, while the bars on the right hand side depict oxyhemoglobin treated samples. Samples were exposed to 60 mM $K^+$ to induce constriction, and were subsequently treated with 1 mM diltiazem ($1^{st}$ bar) or with 1 mM diltiazem and 220 nM SNX-482 ($2^{nd}$ bar) to reverse constriction. Experimental values are the average of four to five experiments. Error bars show the standard error of the mean.
Figure 10:
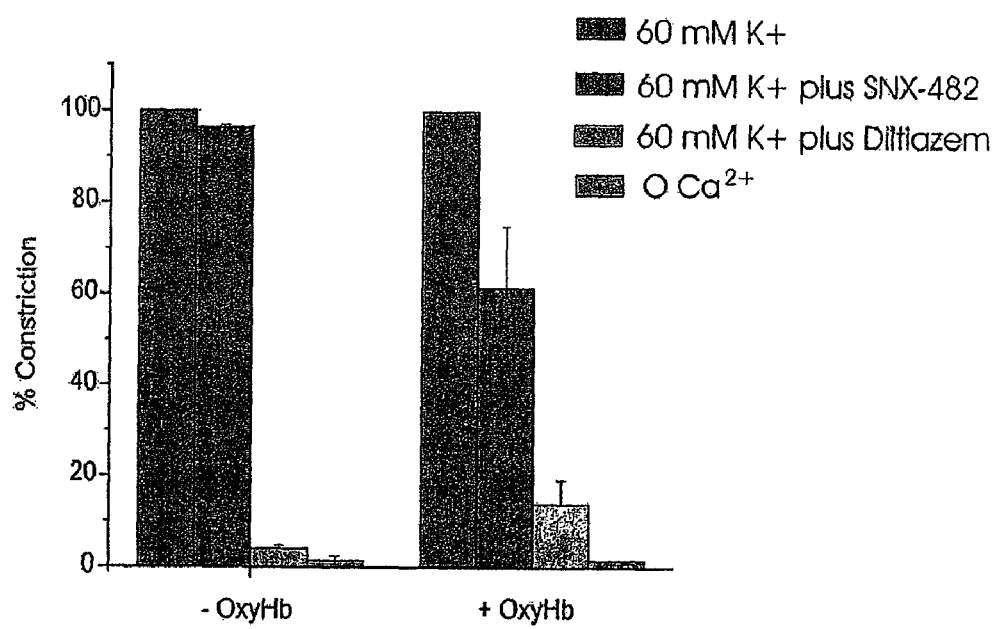
FIG. 10 shows the percentage of residual constriction of the arteries that have been cultured for 5 days under different treatment regimens. The left hand side of the panel shows control treatment, while the bars on the right hand side depict oxyhemoglobin treated samples. Samples were exposed to 60 mM $K^+$ ($1^{st}$ bar), 60 mM $K^+$ and 220 nM SNX-482 ($2^{nd}$ bar), 60 mM $K^+$ and 1 mM diltiazem ($3^{rd}$ bar) and a zero mM extracellular Ca2+ control ($4^{th}$ bar). Experimental values are the average of three to four experiments. Error bars show the standard error of the mean.

To investigate if R-type $Ca^{2+}$ channels are functional in oxyhemoglobin exposed arteries, the arteries were treated with SNX-482, a blocker of R-type $Ca^{2+}$ channels. Arteries organ cultured in the presence of oxyhemoglobin for 5 days were first constricted by 60 mM $K^+$, exposed to 1 mmol/L diltiazem, and then challenged with SNX-482 (220 nmol/L). Unlike arteries cultured in the absence of oxyhemoglobin (left column, FIG. 9), diltiazem could not fully reverse constrictions induced by 60 mmol/L $K^+$. However, this residual constriction observed in the presence of diltiazem was effectively reversed by SNX-482 as shown in the right column in FIG. 9. To examine the possibility that the effect of SNX-482 on vasodilation is dependent on the presence of diltiazem, arteries constricted with 60 mmol/L $K^+$ were exposed to 220 nmol/L SNX-482 in the absence of diltiazem. FIG. 10 shows that SNX-482 alone can dilate cerebral arteries in the absence of diltiazem. Again, the combination of these two drugs completely abolished the constriction. These results clearly indicate that functional R-type VDCC are present in small diameter cerebral arteries treated with oxyhemoglobin for 5 days, which contributes to $K^+$-induced cerebral artery constriction.

Example 7

Oxyhemoglobin Enhances Gene Expression of R-Type VDCC Channels

Figure 11A:
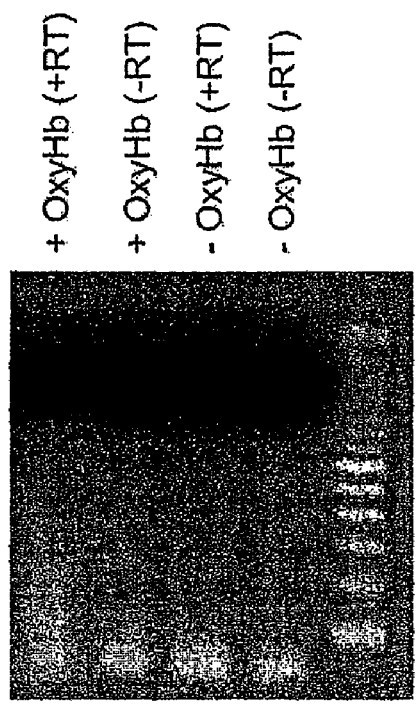
FIG. 11A shows representative results of RT-PCR reactions on control samples and samples treated with oxyhemoglobin. Samples without reverse transcriptase treatment (−RT) are included as a negative control. The band at 435 bp shows the existence of CaV2.3 mRNA.
Figure 11B:
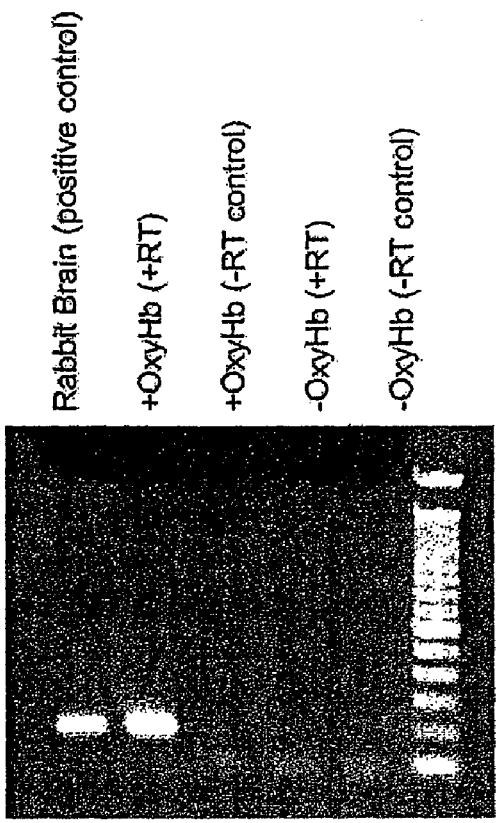
FIG. 11B shows representative results of nested PCR reactions on control samples and samples treated with oxyhemoglobin. Negative control samples (−RT) are also included. The band at 161 bp shows the existence of CaV2.3 mRNA.

The upregulation of R-type $Ca^{2+}$ channels in cerebral arteries was examined by investigating RNA levels of CaV2.3, a pore-forming α1 subunit of R-type VDCC, by RT-PCR. In the absence of oxyhemoglobin, CaV2.3 message was not detected in arteries cultured for 5 days (n=5). However, in arteries cultured with oxyhemoglobin, CaV2.3 mRNA was found in 3 out of 5 preparations, although the intensity of these bands were relatively faint (FIG. 11A). The low amplification of CaV2.3 is not due to the low quantity or quality of RNA isolated from the organ cultured arteries, as GAPDH was clearly amplified in arteries organ cultured for 5 days in the presence or absence of oxyhemoglobin. Nested PCR, a highly sensitive method to detect low levels of gene expression by utilizing two rounds of PCR, was used to confirm the selective expression of CaV2.3. Here, the first round PCR product, as amplified using primers targeting a region that is unique to CaV2.3, was employed as a template for the second round PCR. Using nested PCR, expression of R-type $Ca^{2+}$ channels after 5 days treatment with oxyhemoglobin was seen in five out of five preparations examined (FIG. 11B). In arteries organ cultured in the absence of oxyhemoglobin, a PCR band corresponding to CaV2.3, was observed in one out of five samples. DNA analysis confirmed that the sequence of these bands perfectly matches the CaV2.3 sequence in published database (GenBank Accession number X 67855). These results demonstrate that oxyhemoglobin is indeed able to induce R-type VDCC gene expression.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A method for treating cerebral vasospasm, comprising: administering to a subject in need thereof an effective amount for treating cerebral vasospasm of an R-type voltage-dependent calcium channel inhibitor, wherein the R-type voltage-dependent calcium channel inhibitor is an expression inhibitor, and wherein the expression inhibitor is an antisense oligonucleotide or siRNA molecule.

2. The method of claim 1, wherein the R-type voltage-dependent calcium channel inhibitor is administered within 96 hours after subarachnoid hemorrhage has occurred.

3. The method of claim 1, wherein the R-type voltage-dependent calcium channel inhibitor is administered within 1 week after subarachnoid hemorrhage has occurred.

4. The method of claim 1, wherein the R-type voltage-dependent calcium channel inhibitor is administered during surgery to treat subarachnoid hemorrhage.

5. The method of claim 1, wherein the R-type voltage-dependent calcium channel inhibitor is administered intravenously.

6. The method of claim 1, wherein the R-type voltage-dependent calcium channel inhibitor is administered during surgery.

7. The method of claim 1, wherein the subject does not have symptoms of cerebral vasospasm.

8. The method of claim 1, wherein the subject has symptoms of cerebral vasospasm.

9. A method for treating cerebral vasospasm, comprising: administering to a subject in need thereof an effective amount for treating cerebral vasospasm of an R-type voltage-dependent calcium channel inhibitor, wherein the R-type voltage-dependent calcium channel inhibitor is an expression inhibitor, wherein the R-type voltage dependent calcium channel inhibitor is administered by infusion into cerebrospinal fluid, and wherein the R-type voltage dependent calcium channel inhibitor is an antisense oligonucleotide.

10. The method of claim 9, wherein the R-type voltage-dependent calcium channel inhibitor is administered within 96 hours after subarachnoid hemorrhage has occurred.

11. The method of claim 9, wherein the R-type voltage-dependent calcium channel inhibitor is administered within 1 week after subarachnoid hemorrhage has occurred.

12. The method of claim 9, wherein the R-type voltage-dependent calcium channel inhibitor is administered during surgery to treat subarachnoid hemorrhage.

13. The method of claim 9, wherein the R-type voltage-dependent calcium channel inhibitor is administered during surgery.

14. The method of claim 9, wherein the subject does not have symptoms of cerebral vasospasm.

15. The method of claim 9, wherein the subject has symptoms of cerebral vasospasm.

* * * * *

```
                        SEQUENCE LISTING

<160> NUMBER OF SEQ ID NOS: 21

<210> SEQ ID NO 1
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1
ccccaggaaa tcatcgcc                                                 18

<210> SEQ ID NO 2
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 2
gtcctcagtg ctactcagc                                                19

<210> SEQ ID NO 3
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 3
aatgccaaca acactgccc                                                19

<210> SEQ ID NO 4
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 4
cttcggaaat caagaccgc                                                19

<210> SEQ ID NO 5
<211> LENGTH: 41
<212> TYPE: PRT
<213> ORGANISM: Hysterocrates gigas

<400> SEQUENCE: 5

Gly Val Asp Lys Ala Gly Cys Arg Tyr Met Phe Gly Gly Cys Ser Val
1               5                   10                  15

Asn Asp Asp Cys Cys Pro Arg Leu Gly Cys His Ser Leu Phe Ser Tyr
            20                  25                  30

Cys Ala Trp Asp Leu Thr Phe Ser Asp
        35                  40
```

<210> SEQ ID NO 6
<211> LENGTH: 60
<212> TYPE: PRT
<213> ORGANISM: Dendroaspis polylepis

<400> SEQUENCE: 6

Arg Ile Cys Tyr Ile His Lys Ala Ser Leu Pro Arg Ala Thr Lys Thr
1               5                   10                  15

Cys Val Glu Asn Thr Cys Tyr Lys Met Phe Ile Arg Thr Gln Arg Glu
            20                  25                  30

Tyr Ile Ser Glu Arg Gly Cys Gly Cys Pro Thr Ala Met Trp Pro Tyr
        35                  40                  45

Gln Thr Glu Cys Cys Lys Gly Asp Arg Cys Asn Lys
    50                  55                  60

<210> SEQ ID NO 7
<211> LENGTH: 60
<212> TYPE: PRT
<213> ORGANISM: Dendroaspis angusticeps

<400> SEQUENCE: 7

Trp Gln Pro Pro Trp Tyr Cys Lys Glu Pro Val Arg Ile Gly Ser Cys
1               5                   10                  15

Lys Lys Gln Phe Ser Ser Phe Tyr Phe Lys Trp Thr Ala Lys Lys Cys
            20                  25                  30

Leu Pro Phe Leu Phe Ser Gly Cys Gly Gly Asn Ala Asn Arg Phe Gln
        35                  40                  45

Thr Ile Gly Glu Cys Arg Lys Lys Cys Leu Gly Lys
    50                  55                  60

<210> SEQ ID NO 8
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 8
gagcagcgac aacacctac                                            19

<210> SEQ ID NO 9
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 9
gctggtggag agaagttgc                                            19

<210> SEQ ID NO 10
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 10
acccctcgtc ctgtcctcac                                           20

<210> SEQ ID NO 11
<211> LENGTH: 20

```
<212> TYPE: DNA
<213> ORGANISM: Artificial sequence
<220> FEATURE:
<223> OTHER INFORMATION: Synthetic oligonucleotide

<400> SEQUENCE: 11
tgctctcggt ggtgaccttg                                              20

<210> SEQ ID NO 12
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 12
cgagggtgtg gggaaagag                                               19

<210> SEQ ID NO 13
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 13
cggtggtgac cttgtctgtg                                              20

<210> SEQ ID NO 14
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 14
ccacctgtgc tgtccctgcc ac                                           22

<210> SEQ ID NO 15
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 15
actcgggcca gccagctccc tccac                                        25

<210> SEQ ID NO 16
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 16
gccagaccct cccttccc                                                18

<210> SEQ ID NO 17
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 17
actcagcagg tcgcccacag cgccac                                       26
```

```
<210> SEQ ID NO 18
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 18
gccatctgca tgctgctct                                          19

<210> SEQ ID NO 19
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 19
gccagccatg gcggctccc                                          19

<210> SEQ ID NO 20
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 20
aagcccgctg gagtgcctct                                         20

<210> SEQ ID NO 21
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 21
ctcttccagc tgctgcttct ccc                                     23
```